United States Patent
Cai et al.

(10) Patent No.: US 7,993,638 B2
(45) Date of Patent: Aug. 9, 2011

(54) CANCER TREATMENT COMBINING LYMPHODEPLETING AGENT WITH CTLS AND CYTOKINES

(75) Inventors: Zeling Cai, San Diego, CA (US); Ann Moriarty, Poway, CA (US); Per A. Peterson, Rancho Santa Fe, CA (US); Jon M. Richards, Glenview, IL (US)

(73) Assignee: Janssen Pharmaceutica NV (BE)

( * ) Notice: Subject to any disclaimer, the term of this patent is extended or adjusted under 35 U.S.C. 154(b) by 45 days.

(21) Appl. No.: 12/281,197

(22) PCT Filed: Feb. 23, 2007

(86) PCT No.: PCT/US2007/004841
§ 371 (c)(1),
(2), (4) Date: Jun. 3, 2009

(87) PCT Pub. No.: WO2007/103009
PCT Pub. Date: Sep. 13, 2007

(65) Prior Publication Data
US 2009/0324539 A1    Dec. 31, 2009

Related U.S. Application Data

(60) Provisional application No. 60/778,516, filed on Mar. 1, 2006.

(51) Int. Cl.
*A61K 38/19* (2006.01)
*A61K 38/20* (2006.01)
*A61K 38/21* (2006.01)
*A61K 35/12* (2006.01)

(52) U.S. Cl. .................... 424/85.2; 424/85.7; 424/93.71

(58) Field of Classification Search .................. None
See application file for complete search history.

(56) References Cited

U.S. PATENT DOCUMENTS

| | | |
|---|---|---|
| 4,690,915 A | 9/1987 | Rosenberg |
| 4,844,893 A | 7/1989 | Honsik |
| 6,225,042 B1 | 5/2001 | Cai et al. |
| 6,355,479 B1 | 3/2002 | Webb et al. |
| 2004/0071671 A1* | 4/2004 | Leturcq et al. ............ 424/93.21 |

FOREIGN PATENT DOCUMENTS

| | | |
|---|---|---|
| WO | WO95/22561 | * 8/1995 |
| WO | WO 01/82963 | 11/2001 |
| WO | WO 03/057823 | 7/2003 |

OTHER PUBLICATIONS

Dannull et al (Journal of Clinical Investigation, Dec. 2005, vol. 115, pp. 3623-3633.*
Barnett, Brian et al. "Regulatory T Cells in Ovarian Cancer: Biology and Therapeutic Potential", American Journal of Reproductive Immunology. New York, 1989, vol. 54, No. 6, Dec. 2005, pp. 369-377, XP002586724.
Koopmans, et al. "Porcine Fetal Ventral Mesencephalic Cells are Targets for Primed Xenoreactive Human T Cell Transplantation", 2006, vol. 15, pp. 381-387.
Sun, et al. "The Interaction Defect of Accessory Molecules is Responsible for the Poor Ex Vivo Response to Human Antigens of Mouse T Helper Cells", 2003, Scandanavian Journal of Immunology, vol. 58, pp. 59-66.
Patel, et al. "Class II MHC/Peptide Complexes Are Released from APC and are Acquired by T Cell Responders During Specific Antigen Recognition", 1999, vol. 163, pp. 5201-5210.
Barzaga-Gilbert, et al. "Species Specificity and Augmentation of Responses to Class II Major Histocompatability Complex Molecules in Human CD4 Transgenic Mice", Journal of Experimental Medicine, 1992, vol. 175, pp. 1707-1715.

* cited by examiner

*Primary Examiner* — Karen A Canella

(57) ABSTRACT

In a cancer treatment combining cell therapy with chemotherapy, autologous $CD8^+$ T cells are obtained from a patient, activated ex vivo by contacting them with xenogenic antigen presenting cells loaded with selected peptide antigen, thereby generating antigen-specific activated cytotoxic T lymphocytes. Such activated CTLs are administered to the patient in conjunction with a lymphodepletion and CTL maintenance regimen comprising a non-myeloblative but lymphdepleting agent, such as cladribine or denileukin diftitox, and interleukin-2 and interferon-$\alpha$-2b stimulatory cytokines.

7 Claims, 2 Drawing Sheets

Figure 1: Cytolytic Activity of CTLs Generated *Ex Vivo* Versus Peptide-Loaded Target Cells

CANCER TREATMENT COMBINING LYMPHODEPLETING AGENT WITH CTLS AND CYTOKINES

CROSS REFERENCE TO RELATED APPLICATIONS

This application is the national stage of PCT Application No. PCT/US2007/004841, filed Feb. 23, 2007, which claims priority from U.S. Provisional Application No. 60/778,516, filed Mar. 1, 2006, the entire disclosures of which are hereby incorporated in their entirely.

FIELD OF THE INVENTION

The invention relates to methods for treating cancer in patients involving the administration of activated cytotoxic T lymphocytes, cytokines such as IL-2 and IFN-alpha-2b, and cladribine or denileukin diftitox as a lymphodepleting agent.

BACKGROUND OF THE INVENTION

To facilitate an appreciation of the invention, this section may discuss the historical and technical background leading to the development of the invention, including observations, conclusions, and viewpoints that may be unique to an inventor. Accordingly, the background statements herein should not be construed as an admission regarding the content of the prior art.

A number of therapies have been developed to treat a variety of cancers. Many of these efforts have centered around chemotherapeutic regimens. In one particular combination chemotherapy regimen designed as a treatment for metastatic melanoma, response rates of 35-50% were reported with the "Dartmouth regimen" (a of combination DTIC, cisplatin, BCNU and tamoxifen), but the duration of survival has remained at 6 to 10 months. High rates of remission also have been reported for aggressive high-dose intensity chemotherapy[1] and repletion of hematopoeisis with autologous bone marrow transplants. Nevertheless, the median duration of survival was short, approximately four months[2].

Significant improvements in survival on the order of several years have been noted in a small percentage of melanoma patients undergoing certain immunotherapies. This includes active specific immunotherapy with cancer vaccines, as well as the use of nonspecific boosters of the immune system, such as interleukin-2 (IL-2) and interferon-alpha (IFN-α).[3-5]

The identification of T-cell defined tumor antigens in melanoma has led to clinical trials that target cancer cells by attempting to augment the antigen-specific cellular immune response. This approach has been pursued in numerous vaccination strategies in which the antigens are delivered in an immunogenic context in an attempt to induce potent T cell responses in vivo. Although some clinical responses have been observed in the vaccine trials, the magnitude of the induced T-cell response has generally been low, or undetectable and correlated poorly with clinical responses. Immunization of melanoma patients with cancer antigens may increase the number of circulating CTL precursors; however it has not correlated with clinical tumor regression, suggesting a defect in function or activation in vivo.

Studies in mouse tumor models have demonstrated that adoptive immunotherapy, which involves in vitro immunization of T cells specific for one or more tumor antigens, may be efficacious with minimal toxicity. An obstacle in applying this strategy to the treatment of human tumors has been the identification of immunogenic antigens that render the tumor cells susceptible to CTL-mediated destruction. The isolation of tumor-reactive T cells from melanoma patients has led to the identification of some of the tumor antigens (epitopes) to which CTLs are directed. These include tyrosinase, MART-1/Melan A, gp100, and MAGE. Of these, tyrosinase and MART-1 are nearly universally expressed on melanoma and therefore represent a desired target choice for adoptive immunotherapy.[6-13]

Adoptive T cell therapy involves the removal of T cells from the host environment where tolerogenic mechanisms are active in vivo in cancer patients and contributes to the ineffective responses demonstrated in this patient population. CD8+ T cells may be stimulated ex vivo to generate antigen-specific CTLs (see, e.g., U.S. Pat. No. 6,225,042). Early adoptive immunotherapy approaches used activated lymphocytes as a treatment for various cancers.[14] Initially, lymphokine-activated killer cells (LAK), and later tumor-infiltrating lymphocytes (TIL), activated ex vivo with IL-2, were used, but the demonstration of efficacy was equivocal. These early, controlled clinical trials failed to show an advantage to the use of the ex vivo-activated cells over the direct administration of IL-2 to melanoma patients. More recent studies by Yee et al. (Fred Hutchinson Cancer Research Center)[15] and Dudley et al. (NCI)[16] have demonstrated the potential for certain adoptive T-cell therapeutic approaches. These studies involved use of either T-cell clones specific for MART-1 or gp100 and low-dose IL-2, or TILs expanded ex vivo with allogeneic feeder cells and high-dose IL-2. These studies confirmed that adoptive immunotherapy holds promise as a treatment of cancer, although its full development has been impeded by the lack of reproducible methods for ex vivo generation of therapeutic numbers of antigen-specific CD8+ CTLs.[17]

Cytotolytic CD8+ T cells are a major line of defense against viral infections. CD8+ lymphocytes specifically recognize and lyse host cells that are infected with a virus. Although it would be desirable to harness the cytotoxic activity of CTLs, few in vitro/ex vivo procedures have been available to specifically activate CTLs. The identification of key melanoma-associated antigens and a method for specific in vitro activation of CTLs, allows for an efficient evaluation of adoptive immunotherapy for metastatic melanoma.[15-18]

While it is possible to use naturally occurring antigen presenting cells (APCs) for CD8+ activation in vitro (e.g., dendritic cells, macrophages, autologous tumor cells), the efficiency of activation is low since the MHC Class I molecules of native APCs contain many other peptide epitopes, thus allowing minimal presentation of tumor-associated peptide epitopes. Most of these presented peptides represent normal, innocuous endogenous proteins. A more direct approach to this problem would be to activate CD8+ T cells specifically to those epitopes relevant to combating the disease, in this particular case, melanoma-associated antigens.

Recently, an artificial APC has been developed utilizing a *Drosophila melanogaster* (fruit fly) embryonic cell line, which expresses the major histocompatibility complex (MHC) Class I molecules.[18,19] See also U.S. Pat. Nos. 6,225,042 and 6,355,479. Since the insect *Drosophila* lacks an advanced immune system, the TAP-1,2 peptide transporters, which are involved in the loading of peptide epitopes into the human Class I molecules, are absent. As a result, the transfected Class I molecules appear on the *Drosophila* cell surface as empty vessels. By incubating these transfected *Drosophila* cells with exogenous synthetic peptides that bind to the specific Class I molecules (i.e., tumor antigen T-cell peptide epitopes), all of the available Class I molecules may be occupied with MHC-restricted, specific peptide epitope(s). The high density expression of the Class I molecules presenting single or multiple epitopes, and the addition of key co-stimulatory molecules B7-1 (CD80), CD70, LFA-3 (CD58), and ICAM-1 (CD54) on these *Drosophila* APCs may permits the in vitro generation of potent, autologous cytotoxic CD8+ T cells, which are specific for the antigenic peptides.[20]

SUMMARY OF THE INVENTION

Various general aspects and preferred embodiments of the invention are reflected in the claims appended to this specification, which are incorporated by reference herein. Other preferred embodiments, features, and advantages of the various aspects of the invention will become apparent from the detailed description below taken in conjunction with the drawing figures.

DETAILED DESCRIPTION OF THE INVENTION AND ITS PREFERRED EMBODIMENTS

Figure 1:
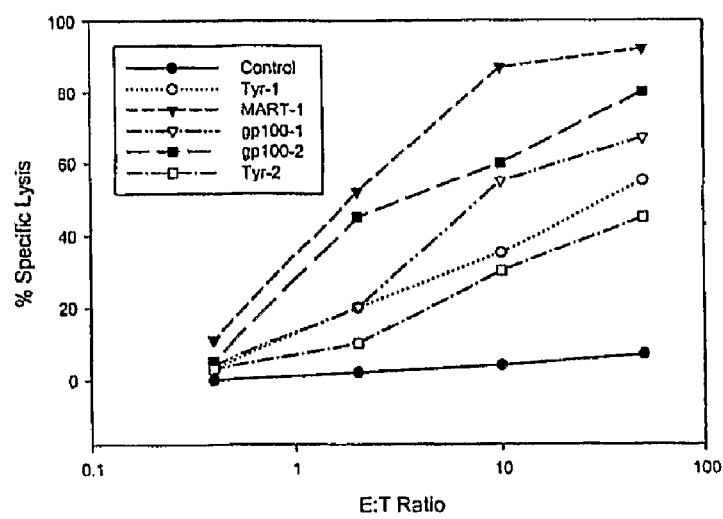
FIG. 1 illustrates cytolytic activity of CTLs generated ex vivo directed against peptide-loaded target cells. CD8+ T cells isolated from a melanoma patient were immunized in vitro with *Drosophila* APCs loaded with five different melanoma-associated peptide epitopes. The activated CD8+ T cells were cultured in vitro using IL-2 and IL-7 to selectively expand the melanoma-specific CTLs. Activity was assessed as specific lysis of $^{51}$Cr-labeled T2 target cells individually loaded with each peptide (Tyr-1$_{689}$, Tyr-2$_{792}$, gp100-1$_{817}$, gp100-2$_{853}$, or MART-1$_{819}$ versus T2 cells loaded with an HLA-A2 control peptide).

The various aspects of the invention are illustrated below through detailed description of specific and preferred embodiments. For the sake of brevity, the disclosures of all patents and other publications cited herein are incorporated by reference. Unless defined otherwise herein or apparent from the context, all technical and scientific terms used herein have the same meaning as commonly used in the art.

The terms "including", "comprising", and "containing" are used herein in their open, non-limiting sense.

The therapeutic regimens of the invention, which comprise administering CTLs that have been activated by contacting xAPCs loaded with selected peptide in conjunction with cytokines and at least one lymphodepleting agent selected from cladribine and DAB-IL2 may be employed to treat cancer in a subject in need of such treatment. Preferably, the cancer is selected from malignant melanoma, multiple myeloma, prostate cancer, lymphoma, non-Hodgkin's lymphoma, leukemia, acute lymphoblastic leukemia, acute myeloid leukemia, chronic lymphocytic leukemia, chronic myeloid leukemia, Burkitt's lymphoma, thyroid cancer, uterine cancer, kidney cancer, ovarian cancer, lung cancer, breast cancer, liver cancer, pancreatic cancer, prostate cancer, colon cancer, skin cancer, stomach cancer, and cervical cancer.

Thus, in one preferred embodiment the invention provides an adoptive CTL therapy regimen for treating or ameliorating a metastatic melanoma comprising: obtaining naïve CD8+ T cells from a subject; contacting the naïve CD8+ T cells with xenogenic antigen presenting cells (xAPCs) that have been loaded with selected peptide antigen, thereby generating activated CTLs that target cells expressing the selected peptide antigen; administering the activated CTLs back to the subject; administering at least one lymphodepleting agent selected from cladribine and DAB-IL2; and administering at least two cytokines that effect CTL persistence. The adoptive CTL therapy regimen preferably employs autologous CD8+ T cells that are activated ex vivo, which when activated and administered to a subject in accordance with the invention are capable of in vivo destruction of tumor cells bearing cancer-associated antigenic epitopes, The term "subject" in this context refers to a mammalian patient in need of treatment for a cancer. For example, a subject may be a human diagnosed with a melanoma, such as an advanced malignant metastatic melanoma, e.g., a patient who has been diagnosed to be HLA-A2 positive and have Stage III/IV unresectable disease.

The CTL agent is prepared from xAPCs. Exemplary xenogenic antigen presenting cells (xAPCs) that are suitable for use may include the following components: an exogenous MHC I molecule; one or more exogenous assisting molecules to assist in the activation of naïve T cells; and host cells capable of expressing the exogenous molecules their surface. Preferably, the exogenous molecules are encoded by xenogenic nucleic acid that has been introduced into host cells. The xAPCs preferably also express exogenous co-stimulator and adhesion molecules, which potentiate T cell activation capability of the xAPCs. Preferably, the host cells are insect cells, more preferably *Drosophila* cells, such as Schneider 2 (S2) cells. Exemplary xAPCs and methods for their manufacture are described in, for example, U.S. Pat. Nos. 6,225,042 and 6,355,479.

The xAPCs may be loaded with peptide antigen by a variety of methods known or available in the art. Peptides are selected that are capable of binding to the empty MHC Class I molecules. Selected peptides preferably correspond to epitopes comprising antigenic or immunogenic amino acid sequences derived from protein expressed on the surface of cells, which will serve as targets for the T cells employed in the adoptive CTL therapy. In order to load empty MHC Class I molecules with selected peptide, one or more antigenic or immunogenic peptide species that binds to such empty MHC Class I molecules may be contacted with the xAPCs under suitable conditions for the binding to occur.

One or more antigenic or immunogenic peptide species may be selected. If more than one species is selected, they may be contacted with the xAPCs simultaneously or at distinct instances, resulting in multi-antigenic or multi-immunogenic MHC-peptide complexes produced on the xAPCs.

Loading of the selected peptide onto empty MHC molecules preferably occurs under conditions that approximate biological binding conditions, which may be approximated in vitro, ex vivo, or in vivo. In selecting peptides, the artisan may consider one or more factors such as thermodynamic, electrostatic, energetic, and entropic considerations, as well as specific amino acids within selected peptides that are required for efficacious binding to MHC molecules.

Preferred peptides include, for example, the peptides corresponding to amino acid sequences selected from a tyrosinase protein, a gp100 protein, and a MART-1 protein. Other preferred peptides include YMNGTMSQV (SEQ ID NO:1), YMDGTMSQV (SEQ ID NO:2), AAGIGILTV (SEQ ID NO:3), ITDQVPFSV (SEQ ID NO:4), YLEPGPVTA (SEQ ID NO:5), and KTWGQYWQV (SEQ ID NO:6). Additional exemplary peptides that may be selected include, for example, the following amino acid sequences, where the protein from which each peptide is derived is noted parenthetically: SILSLKEAST (C-Lectin; SEQ ID NO:70), KMASRSMRL (C-Lectin; SEQ ID NO:71), ALALAALLVV (Pec 60; SEQ ID NO:72), ALLVVDREV (Pec60;

SEQ ID NO:73), YMNGTMSQV (Tyrosinase; SEQ ID NO:74), YMDGTMSQV (Tyrosinase; SEQ ID NO:75), ITDQVPFSV (gp100; SEQ ID NO:7), YLEPGPVTA (gp100; SEQ ID NO:8), AAGIGILTV (MART-1; SEQ ID NO:9), ELAGIGILTV (MART-1; SEQ ID NO:10), CLTSTVQLV (Her-2/neu; SEQ ID NO:11), HLYQGCQVV (Her-2/neu; SEQ ID NO:12), KIFGSLAFL (Her-2/neu; SEQ ID NO:13), IISAVVGIL (Her-2/neu; SEQ ID NO:14), PLTSIISAV (Her-2/neu; SEQ ID NO:15), VMAGVGSPYV (Her-2/neu; SEQ ID NO:16), VLVKSPNHV (Her-2/neu; SEQ ID NO:17), ELVSEFSRM (Her-2/neu; SEQ ID NO:18), YLSGANLNL (CEA; SEQ ID NO:19), GPLTPLPV (AES; SEQ ID NO:20), SLLMWITQC (NY-ESO-1; SEQ ID NO:21), KALFAGPPV (CA-125; SEQ ID NO:22), YLETFREQV (CA-125; SEQ ID NO:23), GLQSPKSPL (CA-125; SEQ ID NO:24), VLLKLRRPV (CA-125; SEQ ID NO:25), ELYIPSVDL (CA-125; SEQ ID NO:26), SLLMWITQV (NY-ESO-1; SEQ ID NO:27), ILAKFLHWL (Telomerase; SEQ ID NO:28), STAPPVHNV (MUC-1; SEQ ID NO:29), FLWGPRALV (MAGE-3; SEQ ID NO:30), FMWGNLTLA (CA-125; SEQ ID NO:31), RLVDDFLLV (Telomerase; SEQ ID NO:32), HLSTAFARV (G250; SEQ ID NO:33), QLSLLMWIT (NY-ESO-1; SEQ ID NO:34), ELWTHSYKV (FBP; SEQ ID NO:35), KVAELVHFL (MAGE-3; SEQ ID NO:36), YIFATCLGL (MAGE-3; SEQ ID NO:37), HLYIFATCL (MAGE-3; SEQ ID NO:38), MLMAQEALAFL (CAMEL; SEQ ID NO:39), STLEKINKT (SSX-4; SEQ ID NO:40), KASEKIFYV (SSX-2; SEQ ID NO:41), SLLMWITQCFL (NY-ESO-1; SEQ ID NO:42), ELTLGEFLKL (Survivin; SEQ ID NO:43), LTLGEFLKL (Survivin; SEQ ID NO:44), SLLEKREKT (SP17; SEQ ID NO:45), TLGEDDPWL (SART-1; SEQ ID NO:46), KLGLKPLEV (SART-1; SEQ ID NO:47), YLWTSAKNT (SCP-1; SEQ ID NO:48), STAPPAHGV (MUC-1; SEQ ID NO:49), GMGSEELRL (LIVIN; SEQ ID NO:50), SLGSPVLGL (LIVIN; SEQ ID NO:51), YLFFYRKSV (hTRT; SEQ ID NO:52), CQQEETFLL (CA-125; SEQ ID NO:53), TLAKFSPYL (PRAME; SEQ ID NO:54), NLTHVLYPV (PRAME; SEQ ID NO:55), STFKNWPFL (Survivin; SEQ ID NO:56), SLLQHLIGL (PRAME; SEQ ID NO:57), FLDQRVFFV (gp100; SEQ ID NO:58), FLDQRVFVV (gp100; SEQ ID NO:59), FLDQVAFVV (gp100; SEQ ID NO:60), GLDREQLYL (MUC-16; SEQ ID NO:61), VMQHLLSPL (MUC-16; SEQ ID NO:62), QQTHGITRL (MUC-16; SEQ ID NO:63), LQPLSGPGL (MUC-16; SEQ ID NO:64), TLDRDSLYV (MUC-16; SEQ ID NO:65), QLYLELSQL (MUC-16; SEQ ID NO:66), KVLEYVIKV (MAGE-1; SEQ ID NO:67), KVADLVGFL (MAGE-1; SEQ ID NO:68), and KTWGQYWQV (SEQ ID NO:69).

Selected peptides may be presented to the cells via a variety of means and methods in the art. Selected peptides may be presented in a manner that allows them to enter an intracellular pool of peptides. For example, peptides may be presented via osmotic loading. Preferably, peptides are added to the xAPC system culture medium. The peptides may be added to the culture medium in the form of an intact polypeptide or protein that is subsequently degraded via cellular processes, such as, for example, enzymatic degradation. Alternatively, the intact polypeptide or protein may be degraded via some other means such as chemical digestion (e.g., cyanogen bromide) or proteases (e.g., trypsin and chymotrypsin) prior to addition to the xAPC system culture medium. Alternatively, an entire protein or polypeptide sequence may be cloned into an appropriate vector and inserted into a prokaryotic cell, whereby the cell generates significant amounts of the antigenic polypeptide that are then harvested, purified, and digested into peptides that are then added to the xAPC system culture medium.

A sufficient amount of each selected peptide may be added to the cell culture to allow the Class I MHC molecules to bind and subsequently present a large density of the peptide on the surface of human Class I MHC-expressing cells.

The xAPCs may be assayed for enhanced APC function compared to the APC function of nonxenogenic or endogenous antigen presenting cells. Enhanced APC function may be determined by measuring any of a variety of parameters of $CD8^+$ T cell activation, such as, for example, a degree of one or more cell surface proteins expression, which is indicative of $CD8^+$ T cell activation, such as CD69 cell surface expression, a degree of differentiation, a degree of cyotoxic killing ability, a degree of specific cell lysis, and a degree cytokine production.

Purification of proteins and peptides may be achieved through various techniques that are known in the art, such as immunoaffinity chromatography, affinity chromatography, protein precipitation, buffer exchanges, ionic exchange chromatography, hydrophobic interaction chromatography, size exclusion chromatography. Antigen-stimulated CTLs may be detected or isolated by peptide-MHC pMHC tetramer staining, wherein detected CTLs are specific for a selected peptide presented by the xAPCs.

Peripheral blood leukocytes (PBLs) are obtained from a subject, and preferably substantially purified. Methods for purification of PBLs include, methods emptying Ficoll gradients may be utilized for this purpose. The purified PBLs are then mixed with xAPCs cells preincubated with the appropriate antigenic peptides. Preferably, PBLs are purified by magnetic bead purification systems that are in the art, such as Miltenyi beads (Myltenyi Biotec) and Dynabead systems (Dynal Biotech). PBLs may also be purified via cell sorting procedures, such as with fluorescence assisted cell sorter (FACS)-based methods, or other appropriate cell sorting devices and methodology. Such cell sorting methods or sorting of red blood cells by using green fluorescent protein (GFP) as a marker for various cell-specific proteins.

Naive T cells are incubated in culture with the appropriate xAPCs and loaded with selected peptide for a time period sufficient to activate and further enrich for a population of $CD8^+$ cells. For example, U.S. Pat. No. 4,690,915 describes a method of obtaining large numbers of lymphocytes via lymphocytopheresis. Preferably, the $CD8^+$ cells are activated in an antigen-specific manner. The ratio of resting or precursor $CD8^-$ (effector) cells to antigen-presenting cells may vary from individual to individual and may further depend upon variables such as the amenability of an individual's lymphocytes to culturing conditions and the nature and severity of the cancer. Preferably, however, the lymphocyte:antigen-presenting cell (e.g., *Drosophila* cell) ratio is preferably in the range of about 30:1 to 300:1. For example, in one embodiment, $3 \times 10^7$ human PBL and $1 \times 10^6$ live *Drosophila* cells are admixed and maintained in 20 ml of RPMI 1640 culture medium.

The effector/antigen-presenting culture may be maintained for as long a time as is necessary to activate and enrich for a population of a therapeutically useable or effective number of $CD8^+$ cells. With a maximum specific $CD8^+$ activation level generally being observed after one to ten days of culture, e.g., after five days of culture, a preferred time is from about three to seven days. In one embodiment of the present invention, in vitro activation of $CD8^+$ T cells may be detected within a brief period of time after transfection of a cell line. In one embodiment, transient expression in a transfected cell line capable of activating $CD8^+$ T cells is detectable within 48 hours of transfection. Thus, either stable or transient cultures of transformed cells expressing human Class I MHC molecules are effective in activating CD8⁻ T cells.

Activated cytotoxic T lymphocytes may be effectively separated from the xAPCs (e.g., *Drosophila* cells) using a suitable method known or available in the art. For example, monoclonal antibodies specific for the artificial APCs, for the peptides loaded onto the artificial APCs, or for the CTLs (or a segment thereof) may be utilized to bind their appropriate complementary ligand. Antibody-tagged cells may then be extracted from the stimulator-effector cell admixture by any of a variety of methods in the art, such as, for example, immunoprecipitation and immunoassay methods. Alternatively, a separation step may be omitted completely and the inactivated xAPCs may be left in culture with the activated CTLs.

Therapeutically effective, cytotoxic amounts of the activated CTLs may be selected as suitable for the described in vitro and in vivo use, e.g., in view of the amount and type of cells that are the ultimate target of these CTL cells. The amount will also be selected in view of the condition of the patient and may be determined via consideration of all appropriate factors by the practitioner. Preferably, about $1\times10^6$ to about $1\times10^{12}$, more preferably about $1\times10^8$ to about $1\times10^{11}$, and even more preferably, about $1\times10^9$ to about $1\times10^{10}$, activated CD8⁺ cells are utilized for adult humans, compared to about $5\times10^6$-$5\times10^7$ cells used in mice.

Preferably, the activated CD8⁺ cells, which are CTLs, are harvested as described above from the xAPC culture prior to administration of the CTLs cells to the individual being treated. The cell culture system is preferably not tumorigenic. Therefore, if complete separation of *Drosophila* cells and activated CD8+cells is not achieved, there should be no inherent danger associated with the administration of a small number of *Drosophila* cells.

Naïve CD4⁺ T cells or CD8⁻ T cells, or both CD4⁺ T cells and CD8⁺ T, cells may be preferably extracted from a subject prior to incubation with the xAPC cultures. Subjects may undergo any of a variety of known or available blood cell separation procedures (e.g., leukopheresis) to collect white blood cells.

Naïve T cells may be harvested from a subject prior to the initiation of other treatment or therapy that may interfere with, attenuate, or in any way limit the specific activation of naïve T cells methods and uses as provided in the present invention. For example, in the treatment of an individual with a neoplasia or tumor, a sample of naïve T cells may be obtained prior to the initiation of chemotherapy or radiation treatment and kept in culture. After the naïve T cells are activated with peptide-loaded xAPCs, the naïve T cells may be expanded and activated, and the activated CTLs may be introduced back into the subject. Alternatively, naive T cells may be activated, and the activated CTLs may be introduced back into the subject from whom the naïve T cells were obtained before, after, or in conjunction with other optional forms of treatment, such as chemotherapy or radiation.

The activated CTLs may also be suspended into an appropriate vehicle for delivery and infusion into a subject. Techniques of reintroducing cellular components are known in the art and include procedures such as those exemplified in U.S. Pat. Nos. 4,844,893 and 4,690,915. For example, administration of activated CTLs cells via intravenous infusion may be employed. Multiple infusions may be required, and these infusions may occur over a period of several weeks or longer.

In the treatment regimens of the invention, cytokines are also administered to attain CTL persistence and thereby enhance half-life, activity, potency, and/or selectivity properties of the CTLs that are administered to a subject. Such persistence may result from a direct effect on the CTLs or from an indirect effect that involves upregulation of antigen expression on target cells of the CTLs. Preferred cytokines are IFN-α-2b and IL-2.

Cladribine (2-CdA, Leustatin®) and/or DAB IL-2 (ONTAK®) lymphodepleting agents are also administered in the inventive treatment regimens. These agents are non-myeloablative and elicit a transient immunosuppression in subjects receiving the CTL therapy.

The timing and duration of the administration of each of the CTL, cytokine, and lymphodepleting agents may be selected by the artisan based on routine experimentation and the guidance herein, including the examples below.

To illustrate various aspects and features of the invention, the following examples are provided.

EXAMPLES

Ex-Vivo Preparation of CTLs

Xenogenic APC (xAPC) lines are generated from Schneider S2 cells (S2 cells), which were established in 1969 from several hundred 20- to 24-hr old Oregon-R (wild type) *Drosophila melanogaster* (Oregon-R) embryos (ATCC CRL-1963), according to published procedures (Schneider, J. Embryol. Morph. 27:353-365,1972). The S2 cell line has been deposited with the American Type Culture Collection (CRL10974). The original supply of S2 cells used to derive the cell lines from which the xAPCs derived are obtained from this source. In order to generate xAPCs, S2 cells are transfected with vectors derived from plasmid vector pRMHa-3 (see, e.g., U.S. Pat. No. 6,225,042). One xAPC line, designated clone A, is transfected with vectors encoding HLA-A2.1 Class I, B7.1 and ICAM-1. A second xAPC line, designated clone B, is transfected with vectors encoding HLA-A2.1 Class I, B7.1, B7.2, ICAM-1 and LFA-3. A third xAPC cell line, designated clone C, is transfected with vectors encoding HLA-A2.1 Class I, B7.1, ICAM-1, LFA-3, and CD70. Thus, clone A expresses HLA-A2, B7.1, and ICAM-1, clone B expresses HLA-A2.1 Class I, B7.1, B7.2, ICAM-1 and LFA-3, and clone C expresses HLA-A2.1 Class I, B7.1, ICAM-1, LFA-3, and CD70.B7.2 and LFA-3.

Independent continuous cultures of clone A- and clone B-descended cells are maintained in Schneider's medium supplemented with 10% fetal calf serum and 500 μg/ml geneticin (G418) and are split twice a week with fresh media added during each split to adjust cell density to approximately $1\times10^6$ cells/mL. Approximately one day prior to induction (day −2 to −4; day 0 defined as the day cells are tested for expression of exogenous molecules and are loaded with peptide), 3×T75 flasks are inoculated with a volume of cell suspension maintained in stock cultures equivalent to $1.5\times10^7$ cells/flask. Complete *Drosophila*-SFM medium without G418 is added to bring the volume up to 15 ml/flask. Flasks are then incubated in a chamber at approximately 27° C. On approximately day −1 to −3, cells are then induced by addition of copper sulfate ($CuSO_4$) to a final concentration of 1.0 mM (1:200 dilution of 200 mM stock of $CuSO_4$; 75 μl of $CuSO_4$ for each T75 flask containing 15 ml of cell suspension) and returned to the 27° C. chamber. The induction time lasts for approximately 24 to 72 hours.

On day 0, flasks containing induced cell cultures are checked visually and microscopically for evidence of contamination. Uncontaminated flasks are pooled and viable cells counted. Samples of pooled cell cultures of approximately $6\times10^6$ cells are evaluated by flow cytometry using fluorescence assisted cell sorter (FACS) analysis to determine the level of expression of exogenous molecules. Cell cultures (approximately 1×10$^7$ cells/mL) are then tested to verify expression exogenous HLA-A2.1, B7.1 and ICAM-1 (for clone A cells) or HLA-A2.1, B7.1, B7.2, ICAM-1 and LFA-3 (for clone B cells) prior to peptide loading. Once expression of exogenous molecules is verified, each cell culture is washed by splitting each culture into two sterile 50 ml conical tubes. Each tube is then filled with HYQ SFX-Insect medium (Hyclone) and centrifuged at 1,700 rpm (600×g) for approximately seven minutes to pellet the cells. Supernatants are discarded, and the tubes containing cell pellet are again centrifuged at 1,700 rpm (600×g) for approximately one minute. Supernatants are removed with a fine tipped pipette. Pellets from each split cell culture are then recombined and resuspended in 8 mL of SFX Insect medium to a cell density of approximately 1×10$^7$ cell/mL. Approximately 40 μL of a β2 microglobulin stock solution at 1.0 mg/mL and 24 μL of 1:50 dilution of a stock peptide combo solution at 1.67 mg/mL for each peptide is added to each resuspended culture. Thus, each cell culture suspension contains β2 microglobulin at a final concentration of approximately 5 μg/mL and each selected peptide to be loaded onto xAPCs at a final concentration of approximately 0.1 μg/mL per peptide. Cell cultures are incubated in the suspension containing β2 microglobulin and peptides for at least four hours, and no more than eight hours, with swirling every 30 minutes at room temperature. After the peptide incubation period, approximately 1 mL aliquots of each cell culture are distributed separately into eight polypropylene tubes (Falcon 2006). Any residual cell culture suspension is discarded.

CD8$^+$ cells isolated from leukapheresis samples by positive selection with an anti-CD8 antibody are stimulated against human melanoma-associated peptides (tyrosinase-689$_{369-377}$, tyrosinase-792$_{369-377}$, MART-1-819$_{27-35}$, gp100-817$_{209-217}$, gp100-818$_{280-288}$ and gp100-853$_{154-162}$) presented by *Drosophila* cells expressing human Class I and co-stimulation/adhesion molecules HLA-A2.1, B7.1, CD70, LFA-3 and ICAM-1. CD8$^+$ cells are restimulated for two rounds with autologous monocytes (pulsed with the described epitopes) in the presence of IL-2 and IL-7. The number of effector cells is then increased by non-specific stimulation with anti-CD3 monoclonal antibody in the presence of gamma-irradiated autologous feeder cells and IL-2. Cytotoxic T lymphocyte activity is measured against peptide-loaded T2 cells and a panel of melanoma cells, while the purity of in vitro-stimulated CD8$^+$ T cells is assessed by flow cytometry.

Materials

| Cell Line | Source |
| --- | --- |
| *Drosophila* S2 | ATCC |
| Malme 3 | ATCC (Normal skin fibroblast from a melanoma patient) |
| Malme 3M | ATCC (Metastatic melanoma from lung, same patient as Malme 3) |
| M14 | UCSD; see U.S. Pat. No. 5,208,146 and Cahan et al., PNAS U.S.A. 1982, vol. 79(24), pp. 7629-7633 (HLA-A2.1 human melanoma) |
| 01-KN | J&JPRD; see US 2004-0071671 (Melanoma cell line HLA-A2.1, melanoma antigen negative) |
| K562 | ATCC (Human erythroleukemic cell line; target for NK cells) |
| T2 cells | ATCC (Human B and T lymphoblast hybrid, class II negative) |

Reagents rhIL-7. Recombinant human interleukin-7 (IL-7) is a lymphokine produced in *E. coli* and purified by the supplier (PeproTech) using high performance liquid chromatography (HPLC) but not antibody. IL-7, received as a powder, is diluted in sterile DPBS containing 1% human serum albumin. The bulk solution is then filtered through a 0.2-μm filter, aliquoted (30,000 U/mL, 1000× concentration) into sterile vials, and stored at −80° C. prior to use.

rhIL-2. Recombinant human interleukin-2 (IL-2) is produced by recombinant DNA technology and supplied by Chiron Corporation (Proleukin®). IL-2, received as a powder, is diluted in IL-2 diluent (0.5% human serum albumin in 50 mM acetic acid), filtered through a 0.2-μm filter, aliquoted into sterile vials (20,000 U/mL, 1000× concentration), and then stored at −80° C. prior to use.

Tyrosinase Peptide YMNGTMSQV (SEQ ID NO: 1). A tyrosinase peptide (tyr 369-377), corresponding to amino acids 369-377 of human tyrosinase, is manufactured and purified using GLP compliance standards (Synpep Corporation). The peptide powder as received from the manufacturer (Synpep Corporation) is dissolved in dimethylsulfoxide (DMSO) to achieve a stock peptide solution at a concentration of 10 mg/mL, and is stored at −72° C. to −88° C. prior to use. This stock peptide solution is mixed in equal parts with other peptide stock solutions (also at a concentration of 10 mg/ml) to generate combination peptide solutions for use in loading xAPCs. The combination peptide solutions are aliquoted into sterile vials in a Class 10,000 clean room under aseptic conditions in a Class II biosafety cabinet.

Tyrosinase Peptide YMDGTMSQV (SEQ ID NO: 2). A deamidated form of the tyr 369-377 peptide described above, which contains an aspartic acid residue in place of an asparagine residue at position three of the peptide, is manufactured and purified using GLP compliance standards (Synpep Corporation). This deamidation form is called tyr 369-377d. The peptide powder received from the manufacturer is dissolved in dimethylsulfoxide (DMSO) to achieve a stock peptide solution at a concentration of 10 mg/mL, and is stored at −72° C. to −88° C. prior to use.

gp100 Peptide ITDQVPFSV (SEQ ID NO: 4). A gp100 peptide (gp100$_{209-217}$), corresponding to amino acids 209-217 of human gp-100, is manufactured and purified using GLP compliance standards (Synpep Corporation). The peptide powder is dissolved in dimethylsulfoxide (DMSO) to achieve a stock peptide solution at a concentration of 10 mg/mL, and is stored at −72° C. to −88° C. prior to use.

gp100 Peptide KTWGQYWQV (SEQ ID NO: 6). A gp100 peptide (gp100$_{154-162}$), corresponding to amino acids 154-162 of human gp100, is manufactured and purified using GLP compliance standards. The peptide powder as received from Synpep Corporation is dissolved in dimethylsulfoxide (DMSO) to achieve a stock peptide solution at a concentration of 10 mg/mL, and is stored at −72° C. to −88° C. prior to use.

gp100 Peptide YLEPGPVTA (SEQ ID NO: 5). A gp100 peptide (gp100$_{280-288}$), corresponding to amino acids 280-288 of human gp100, is manufactured and purified using GLP compliance standards by Synpep Corporation. The peptide powder is dissolved in dimethylsulfoxide (DMSO) to achieve a stock peptide solution at a concentration of 10 mg/mL, and is stored at −72° C. to −88° C. prior to use.

MART-1 Peptide AAGIGILTV (SEQ ID NO: 3). A MART-1 peptide (MART1$_{27-35}$), corresponding to amino acids 27-35 of human MART-1, is manufactured and purified using GLP compliance (Synpep Corporation). The peptide powder is dissolved in dimethylsulfoxide (DMSO) to achieve a stock peptide solution at a concentration of 10 mg/mL, and is stored at −72° C. to −88° C. prior to use.

DYNABEADS® M-450. DYNABEADS® M-450 (SAM) IgG are sterile paramagnetic beads coated with polyclonal sheep anti-mouse IgG that bind the primary mouse IgG. DYNABEADS, available from Baxter Oncology Inc., are stored at 4° C. prior to use in T cell isolation using the Isolex 300i Magnetic Cell Selector.

Human Serum Albumin. 25% HSA, USP (Baxter Fenwal Laboratories; the plasma source for each lot tested to be negative for HIV-1 HIV-2, HCV, and HBV), is stored at RT prior to use as a source of buffered protein during the following T cell preparation and activation steps steps: purification of $CD8^+$ T cells and $CD8^-$ T cells; peptide-loading of adherent cells; and final formulation of activated T cells.

Anti-CD8 Antibody. Anti-CD8 monoclonal antibody (37B1A) is a murine monoclonal antibody directed against the CD8 antigen of T cells, which is used to select $CD8^+$ T cells with the Isolex 300i Magnetic Cell Selector System. The concentrate solution is diluted in sterile DPBS for use in $CD8^+$ T cell isolation or activation processes. The bulk solution is filtered through a 0.2-μm filter and then aliquoted into single-use vials in a Class 10,000 clean room under aseptic conditions in a Class II biosafety cabinet. Aliquots (10.0 mg/mL) are stored at −80° C. prior to use.

CD8 Alpha Chain Peptide -AAEGLDTQRFSG (SEQ ID NO: 76). CD8 alpha light chain peptide (AAEGLDTQRFSG (SEQ ID NO: 76)) is purified and manufactured under GLP compliance standards. The CD8 alpha chain peptide is used in $CD8^+$ T cell isolation processes to release $CD8^+$ T cells captured using CD8 (37B1A) antibody and the Isolex 300i Magnetic Cell Selector. Each lot of peptide is manufactured by Synpep Corporation to meet pharmaceutical grade standards, and is tested for peptide sequence, purity, molecular weight, and appearance. The CD8 alpha chain peptide, received as a powder, is further processed to create a stock solution of 10 mg/ml. This stock solution is diluted in DPBS, filtered through a 0.2-μm filter, aliquoted into sterile vials, and stored at −72° C. to −88° C. prior to use. Vialing of the peptide reagent is performed in a Class 10,000 clean room under aseptic conditions in a Class II biosafety cabinet.

Human β2M Microglobulin. A concentrate of human beta-2 microglobulin (β2M) produced by recombinant DNA technology is diluted in sterile DPBS to achieve a concentration of 1.0 mg/mL. The bulk solution is then filtered through a 0.2-μm filter, aliquoted into sterile vials and stored at −80° C. prior to use during the preparation and peptide-loading of xAPCs and peptide loading of adherent cells.

Sodium Citrate Solution. A sterile, nonpyrogenic anticoagulant sodium citrate solution, USP (Baxter Fenwal), is stored at room temperature (RT) prior to use as a buffer additive for running the Isolex 300i Magnetic Cell Selector for selection of $CD8^+$ T cells and $CD8^-$ T cells.

Schneider's Medium. Schneider's *Drosophila* medium is a culture medium used for culturing *Drosophila* cells. Each lot of medium is tested by the supplier (Invitrogen Corporation) for osmolarity, pH, sterility, and the ability to sustain the growth of *Drosophila* cells. Schneider's *Drosophila* medium (1× concentration) is stored at 2° C. to 6° C. prior to use.

Fetal Bovine Serum. Fetal bovine serum (FBS), which is used as a protein source for the growth of host cells or xAPCs cells, is stored at −80° C. The FBS, available from Gemini Bioproducts, is processed from bovine fetal blood from animals of United States origin. The maternal animals from which the blood is derived are free of infectious and contagious diseases and injurious parasites.

HYQ SFX Insect Medium. Hyclone's SFX Insect Medium (Hyclone Corporation) is a serum-free culture medium (1× concentration) used during the peptide loading of xAPCs, and is stored at 2° C. to 6° C. prior to use. This medium does not contain products of bovine origin.

Copper Sulfate. Copper (II) sulfate pentahydrate (Aldrich) is used for induction of modified host cells to express human HLA, co-stimulatory, and adhesion molecules. The stock solution is formulated by dissolving the crystalline $CuSO_4$ in endotoxin-free sterile water to achieve a concentration of 200 mM and aseptically filtering the solution through a 0.2-μm filter into a sterile container in a Class II biosafety cabinet. The filtered stock solution is stored at 2° C. to 6° C. prior to use.

RPMI. RPMI culture medium (available from Invitrogen Corporation or Gibco), which is serum- and antibiotic-free (1× concentration), is used to grow T cells. RPMI culture medium is stored at 2 to 6° C. prior to use.

Dulbecco's Phosphate Buffered Saline (DPBS). Sterile, non-pyrogenic Dulbecco's phosphate buffered saline (DPBS) solution (available from Invitrogen Corporation or Gibco, 1× concentration) is stored at RT prior to use. DPBS is used for the following procedures: running the Isolex 300i Magnetic Cell Selector instrument during the selection of $CD8^+$ T cells and $CD8^-$ T cells; washing non-adherent cells during restimulation steps and washing unbound OKT3 monoclonal antibody during non-specific expansion; and diluting human β2 microglobulin, IL-7, CD8 peptide, and OKT3.

Leibovitz's Medium. Leibovitz's L-15 medium (without L-glutamine; 1× concentration), available from Sigma-Aldrich, is stored at 2° C. to 6° C. prior to use during peptide-loading of the T cell activation process.

OKT®3 Antibody. Orthoclone OKT®3 (1.0 mg/mL), a murine monoclonal antibody specific for the CD3 antigen of T cells supplied in ampoules as a sterile solution approved for clinical use (available from Ortho), is aliquoted into single-use vials under sterile conditions and stored frozen at −80° C. prior to use in the activation of T cells.

Geneticin (G418). Geneticin (Invitrogen Corporation) is a selective antibiotic used in the culture of *Drosophila* cells for maintaining expression of exogenous molecules encoded by xenogenic nucleic acid. Geneticin is supplied as a sterile stock solution (50 mg/mL), and is stored at 2 to 6° C. prior to use.

Calcium Chloride. Calcium chloride hydrate is used for clotting of autologous plasma obtained from the lymphopheresis product to generate autologous serum used in $CD8^+$ T cell isolation or activation processes. Calcium chloride hydrate is received as a crystalline powder, is compounded into a stock solution (1M), and stored at 2° C. to 6° C. prior to use. The stock solution is formulated by dissolving calcium chloride in endotoxin-free sterile water and aseptically filtering through a 0.2-μm filter into a sterile container in a Class II biosafety cabinet.

Acetic Acid. Acetic acid (17.4M) used for the preparation of stock solutions of IL-2 is obtained from Sigma Corporation and stored at RT prior to use.

FICOLL-PAQUE® Plus. Following isolation of $CD8^+$ T cells and $CD8^-$ T cells with the Isolex 300i Cell Selector System, mononuclear cells from the non-$CD8^+$ fraction are further fractionated using FICOLL-PAQUE® Plus (1× concentration), a Ficoll gradient reagent without any animal components available from Amersham Pharmacia Biotech used to remove dead cells, neutrophils, and red blood cells. The reagent is stored at RT prior to use.

PENTASPAN®. PENTASPAN (B. Braun Medical Inc) is a sterile solution of 10% pentastarch in 0.9% sodium chloride for clinical use (NDC 0264-1972-10), and is stored at RT prior to use. It is used (1× concentration) as a cryoprotectant in the cryopreservation of isolated CD8⁻ T cells and CD8⁺ T cells.

Dimethyl Sulfoxide (DMSO). DMSO is used as a cryoprotectant in the cryopreservation of isolated CD8⁻ T cells and CD8⁺ T cells. The DMSO solution (1× concentration), available from Sigma-Aldrich, is stored at RT prior to use.

L-Glutamine. L-Glutamine (USP), 200 mM (100× concentration), available from Invitrogen Corporation, is used as an RPMI culture medium supplement, and is stored at −80° C. prior to use.

MEM Sodium Pyruvate Solution. MEM sodium pyruvate solution (100 mM, 100× concentration), available from Invitrogen Corporation, is used to supplement RPMI medium, and is stored at 2 to 6° C. prior to use.

Non-Essential Amino-Acids. Non-essential amino-acids (10 mM; 100× concentration) from Invitrogen Corporation, used to supplement RPMI medium, are stored at 2 to 6° C. prior to use.

HEPES Solution. 1M (200× concentration) HEPES buffer solution (Invitrogen Corporation), used to supplement RPMI medium, is stored at 2° C. to 6° C. prior to use.

X-Vivo 10-Cell Medium. X-vivo 10-cell culture medium, supplied by BioWhittaker, is stored at 2° C. to 6° C. prior to use. This medium (1× concentration), which is serum-, phenol red-, and antibiotic-free, is used during the phase of non-specific expansion of T cells activated by exposure to peptide-loaded xAPCs.

Sodium Chloride Injection. A 0.9% sodium chloride solution, USP, available from Baxter Fenwal Laboratories, is used for cell washing procedures during harvesting of T cells. The solution, which is sterile, non-pyrogenic, and free of animal components, is stored at RT prior to use.

Dextrose+Sodium Chloride Solution. An injectable solution of 5% dextrose and 0.9% sodium chloride, USP (Baxter Fenwal Laboratories), is obtained as a sterile, non-pyrogenic solution free of animal components. The solution, which is used as a storage buffer for activated T cells, is stored at RT prior to use.

Lactated Ringer's Solution. A 0.9% Lactated Ringer's solution, USP (Baxter Healthcare Laboratories), which is a sterile, low-endotoxin solution of calcium chloride, potassium chloride, sodium chloride, and sodium lactate in water for injection (free of animal components), is stored at RT prior to use in harvesting and suspending T cells.

Distilled Water. Cell culture grade distilled water, which is obtained by membrane-filtering and endotoxin-screening (Invitrogen Corporation), is used as a solvent for the preparation of stock solutions of copper sulfate, calcium chloride, and interleukin-2 (IL-2) and is stored at RT prior to use.

Other Materials.

Lymphopheresis products are collected from human subjects diagnosed with melanoma and are stored at RT prior to use for the generation of an autologous, patient-specific cell product.

Autologous human serum is used as a protein source for culturing of isolated T cells. Autologous human plasma is prepared from lymphopheresis product by adding calcium chloride to achieve fibrin clotting and then collecting the liquid serum phase. The collected liquid serum phase is stored at 4° C. for short-term storage and at −80° C. for long-term storage.

A $Drosophila$ xAPC line, derived from the xenogenic $Drosophila$ clone B, which is used as a seed stock to create a continuous $Drosophila$ xAPC culture, is obtained as described below.

Procedures

Isolation of Human CD8⁺ Cells

CD8⁺ cells are isolated from leukapheresis samples using an Isolex 300i machine (Baxter) by positive selection with an anti-CD8 monoclonal antibody (antibody1) followed by a Dynabeads™ (Dynal) isolation procedure using sheep anti-mouse IgG (antibody2) coated onto magnetic beads (SAM beads). The anti-human CD8 mouse monoclonal antibody is added to washed cells resuspended in Dulbecco's PBS supplemented with 1% HSA (Baxter-Hyland) and 0.2% sodium citrate. Dynal magnetic beads (Dynabeads™) are added at a bead to cell ratio of 1:1 to 1:2 depending on the number of PBMCs. The isolated CD8⁺ cells are removed by magnetic separation. The remaining non-CD8 fraction is collected and cryopreserved for future use during the restimulation and non-specific expansion steps. Dissociation of the CD8 cell-antibody1-antibody2-bead complex is achieved by incubation at 37° C. for 45 minutes in the presence of CD8 peptide$_{59-70}$ (AAEGLDTQRFSG (SEQ ID NO: 76)), the peptide to which antibody1 was generated. Released beads are removed magnetically and the CD8⁺ cells are counted and analyzed by flow cytometry to evaluate purity. Recovery of CD8⁺ cells is typically greater than 80%. Heat-inactivated serum is prepared by collecting the autologous plasma at the time of the initial cell washing step. Fibrin is clotted using $CaCl_2$ and the fibrin clot removed. Serum is heat-inactivated, filtered, aliquoted and frozen at −80° C. Non-CD8⁺ cells are retained from the positive selection procedure and purified using a Ficoll gradient. These cells are cryopreserved in DMSO, Pentaspan, and heat-inactivated autologous serum and stored in liquid nitrogen ($LN_2$). These cells are used as the source of adherent cells at the time of the restimulations and are peptide-pulsed prior to use as antigen presenting cells.

In vitro Immunization of Purified Human CD8⁺ T Cells

Primary Stimulation. Transfected $Drosophila$ S2 cells are incubated in Schneider's medium (10⁶ cells/mL) supplemented with 10% fetal calf serum and copper sulfate at 27° C. for 24 to 72 hours. S2 cells (clone 1120-3-9) are harvested, washed and resuspended in HYQ SFX-Insect medium (Hyclone) containing 0.1 µg/mL each of human gp100$_{154-162}$, gp100$_{209-217}$, gp100$_{280-288}$, MART-1$_{27-35}$, tyrosinase-N$_{369-377}$ and tyrosinase-D$_{369-377}$ peptides and 5 µg/mL human β2 microglobulin recombinant protein purified from $E. coli$. Following incubation at room temperature (23-25° C.) for four hours, the S2 cells are mixed with CD8⁺ cells at a ratio of 1:10 ($Drosophila$ cells:T cells) in Roswell Park Memorial Institute (RPMI) medium (Gibco) supplemented with 5-10% autologous serum. The cell mixture is incubated at 37° C. during which time the $Drosophila$ cells die off (by 48 hours). On day four, IL-2 (20 U/mL) and IL-7 (30 U/mL) are added to selectively expand the melanoma-specific CTL population.

Restimulations. Autologous, CD8-depleted PBMCs, obtained at the time of lymphapheresis and frozen for future use, are thawed, washed and resuspended at 10⁷ cells/mL in RPMI medium containing 10% autologous serum, 5 µg/mL recombinant human β2 microglobulin and 5 µg/mL of gp100$_{154-162}$, gp100$_{209-217}$, gp100$_{280-288}$, MART-1$_{27-35}$, tyrosinase-N$_{369-377}$ and tyrosinase-D$_{369-377}$ peptides. Following γ-irradiation (5,000 rads), the cells are incubated at 37° C. for two hours in the flasks used for the restimulation. Non-adherent cells are removed by washing with Dulbecco's PBS. Adherent monocytes are loaded with the peptide epitopes and incubated for 90 minutes in Leibovitz medium containing 5 µg/mL human β2 microglobulin in 1% HSA and 5 µg/mL of each peptide. The supernatant is removed and the *Drosophila*-activated CD8$^+$ cell suspension ($2.5\times10^6$ cells/mL in RPMI medium with 10% autologous serum) is added at a ratio of about 10 CD8$^+$ cells to one adherent monocyte. After three to four days of culture at 37° C., IL-2 (20 U/mL) and IL-7 (30 U/mL) are added with a medium change to selectively expand the melanoma-specific CTL population.

Non-specific Expansion. The CD8$^+$ effector cells that have undergone two rounds of restimulation are expanded in cell culture bags along with feeder cells (irradiated autologous non-CD8$^+$ selected cells) after being stimulated with OKT3 antibody. Frozen non-CD8$^+$ selected cells are thawed, washed and then gamma-irradiated (3,500 rads). A ratio of 4:1 (feeder:effector) is placed in T-225 flasks that have been coated with OKT3 antibody. OKT3 stimulation is performed in complete RPMI medium containing 10% autologous serum supplemented with 20 U/mL of IL-2. Two days later, the stimulated T cells are diluted with fresh media (X-vivo 10 medium) and transferred to cell culture bags for expansion. Fresh media and IL-2 are supplemented approximately every two to three days to feed the rapidly expanding T cells.

Preparation and Release of CTLs

Cell Harvest and Final Product Formulation. Harvest of the final cell product is performed by centrifugation to remove culture media and to concentrate the cells. After centrifugation, cells are washed in saline containing 1% human serum albumin (HSA), filtered through a 70-µm filter, and then diluted in infusion medium. The cell product for infusion contains autologous CTLs in 300 mL Lactated Ringer's Injection, USP (76% v/v), 5% Dextrose in 0.9% Sodium chloride (4% v/v) and 25% HSA (20% v/v). Final product cells are packaged in a 1000 mL transfer bag in a chilled insulated shipping container with a temperature data logger.

Product Testing. Tests performed before release of CTL product are listed below. Specific activity directed against individual peptides is assessed by measuring the cytotoxic activity of the effector cells against chromium-labeled T2 cells loaded with each individual peptide used for stimulation. Cytotoxic activity is also measured against chromium-labeled melanoma targets (Malme 3M, M14), using normal fibroblasts (Malme 3) or a melanoma cell line (01-KN) negative for tyrosinase, gp 100 and MART-1 as controls.

Phenotype: A portion of the cell harvest is used to test the phenotype of the CD8 product prior to shipment. The final product specification is CD3, CD8 and TCR expression. Additional phenotypic evaluation for markers consistent with memory, activation, etc. are measured and recorded.

Identity: The HLA-A2, HLA-C and HLA-DR status of the sample is determined by analysis of a DNA preparation isolated from a PBMC sample prepared at the time of receipt of the initial leukapheresis and from the CD8+ T cells collected at the end of the culture, taken from the harvested cell product. PCR analysis of DNA samples is performed with HLA-specific primer oligos provided by Genovision. The final product specification is identity with day 0 sample.

Cell Counts: The desired cell dose for infusion is $10^{10}$ CD8+ T cells. The final product infusion limit is $10^{10}$ cells. The total number of cells generated is patient-dependent. Cell doses averaged $9\times10^9$ in a previous study where the cells were generated under the same ex vivo protocol. The final cell count is made by determining the number of viable cells.

Viability: The viability of the final cell dose is >70%. The number of viable cells is established by microscopically counting cells that exclude trypan blue dye.

Mycoplasma Testing: Testing of the cells for mycoplasma is performed before the cells are administered to the patient to confirm negative mycoplasma detection. The Roche PCR kit is used which also includes an ELISA assay. In addition, samples of the T cell cultures are collected at the first cytokine feeding (day 6) and sent to BioReliance to fulfill the 28-day culture procedure. The results of the culture are received post T cell infusion.

Endotoxin testing: The endotoxin test on the final cellular product is performed using a Limulus Amebocyte Lysate assay (BioWhittaker, Walkersville, Md.). The endotoxin level limit is less than 5 EU/kg infused into the patients. The final cell product specification is <1 EU/mL.

In Process Product Sterility Tests: In process testing for sterility is performed using the BacT/Alert system. Samples are taken during times of media changes. A sample from the final dose is also tested by the BacT/Alert system, and the final product specification is absence of growth.

*Drosophila* DNA and Insect Viral RNA Detection: DNA is isolated from the final CD8+ T cell product and used as a template for a *Drosophila* DNA PCR assay, which uses primers specific for the insect vector used to prepare the recombinant *Drosophila* APCs. This sample is compared to the naïve CD8+ sample that acts as the negative control and *Drosophila* cell DNA is used as the positive control. Total RNA is also isolated from the same CD8+ T cell samples and a quantitative real time RT-PCR, which can detect 20 copies/µg of cDNA of three different, known insect viral RNA viruses, is performed. The product specification for both assays is negative detection of insect genomic and viral nucleic acid.

Lytic Activity: Lytic activity is evaluated for the final CD8+ T cell product by a chromium-release assay in both peptide-loaded T2 cell targets, to measure anti-peptide activity, and established or autologous melanoma cell HLA-A2 targets and donor-matched tumor and non-tumor lines (Malme 3 and Malme 3M) to assess melanoma-specific killing. The product specification is specific killing of target cells.

Also, to facilitate monitoring the following tests may also be performed in addition the release tests described above:

Tetrameric Staining: CD8+ T cells for the naïve leukapheresis-derived sample is evaluated for the presence of antigen-specific T cells with tetrameric molecules which have been designed to enumerate T cells with specificity for the peptide epitopes used to generate the CTLs ex vivo. This allows the monitoring of antigen-specific T cells after treatment.

Melanoma Tumor Cells in Peripheral Blood Samples: Sensitive, quantitative real time PCR assays allow for the monitoring of circulating melanoma cells in patient blood samples, before, during and after drug treatment. While not all stage III/IV melanoma patients demonstrate circulating tumor cells, the detection of these cells can be used as a surrogate marker for response to therapy.

CTL products prepared as described above may be used in the combination therapy treatment regimens of the invention as illustrated by the preferred embodiments described in the following examples.

Treatment of Patients with Metastatic Melanoma Using Autologous CD8$^+$ Lymphocytes Stimulated Ex Vivo with Drosophila Cells Loaded with Melanoma-Associated Peptides (MART-1, gp100, and Tyrosinase) and Subcutaneous Administration of IFNα-2b and IL-2, with and Without Administration of 2-CdA or DAB IL-2

These examples illustrate treatments comprising the administration of autologous cytotoxic T lymphocytes (CTLs) that are specific for peptide epitopes derived from melanoma-associated antigens in combination with a lymphodepletion agent selected from cladribine and DAB IL2 as well as cytokines IL-2 and IFN-α-2b, as well as a control treatment. The cell therapy agent, which comprises autologous CTLs that have been activated such that they specifically target melanoma cells expressing MART-1, gp100, and tyrosinase by contacting Drosophila xAPCs loaded with MART-1-, gp100-, and tyrosinase-derived antigenic peptides, is designed to enhance and maintain a patient's immune targeting of melanoma cells expressing MART-1, gp100, and tyrosinase. The addition of immunomodulators IFN-α-2b and IL-2 is included to augment the response of the CTLs. A non-myeloablative, but lymphocyte-depleting, preparative regimen (cladribine) or a specific T cell subset depletion denileukin diflitox (DAB IL-2) is administered prior to the CTL infusion to enhance the engraftment of the CTLs. The treatment is designed to cause tumor regression and clinical benefit through persistence of melanoma-specific CTLs.

More particularly, clinical patients with advanced, malignant melanoma that are HLA-A2 positive are administered a non-myeloablative, but lymphocyte-depleting, preparative regimen consisting of either cladribine (0.12 mg/kg/day×5 days) or DAB IL-2 (a single injection of 18 µg/kg). In addition, a concomitant regimen of interferon-α-2b (IFN-α-2b; 10 MIU/m$^2$) is administered daily, for 5 consecutive days, by subcutaneous injection prior to CTL infusion. Subsequently, the patients receive a single dose of ex vivo-generated, Drosophila xAPC-stimulated, autologous CD8$^+$ T cells, which display the CTL phenotype. The cell infusion is immediately followed by subcutaneous daily administration of low-dose (e.g., 3 MIU) IL-2, for twenty-eight (28) days, followed by tumor assessment. Subcutaneous, daily administration of low-dose (e.g., 3 MIU) IL-2 is continued in patients without evidence of disease progression.

The CTLs are generated by a method in which purified naïve CD8$^+$ T cells are stimulated with Drosophila xAPCs presenting six different melanoma-associated T cell peptide epitopes in the context of human MHC class I restriction, resulting in CTLs that display multiple specificities for MART-1, gp100, and tyrosinase, after approximately 34 days in culture.

Blood is collected at screening to qualify patients for the study and the preparative leukapheresis procedure takes place on day 0 or day 1. Patients undergo a standard 2.0-3.0× the blood volume leukapheresis to obtain enough white blood cells required to prepare the cell therapy agent. At indicated times, additional leukapheresis procedures (≦of third the amount used to obtain the initial CD8 sample) is be performed to obtain peripheral blood cells for analysis. These samples are used to monitor the presences of antigen-specific T cells and possible circulating melanoma tumor cells. Plasma and blood cells are also collected to meet the xenotransplantation requirement for archiving pre- and post-treatment samples. Leukapheresis products are transported to a facility where CD8$^+$ T cells are isolated, stimulated and cultured for approximately 34 days.

An evaluation of measurable lesions is conducted at both 4 and 8 weeks following the CTL infusion. An objective of the study is to determine whether administration of a full non-myeloablative, lymphocyte-depleting (cladribine) or a selective T cell subset depletion (DAB IL-2), prior to the T-cell infusion and in conjunction with an established immune-enhancing cytokine regimen, will result in antigen-specific T cell persistence with accompanying objective tumor regression.

Preparation of Cytotoxic Lymphocytes

CD8$^+$ cells isolated from leukapheresis samples by positive selection with an anti-CD8 antibody are stimulated with human melanoma-associated antigenic peptides (tyrosinase$_{369-377(native)}$, tyrosinase$_{369-377(modified\ D371)}$, MART-1$_{27-35}$, gp100$_{154-163}$, gp100$_{209-217}$ and gp100$_{280-288}$) presented by Drosophila xAPCs expressing human class I and co-stimulatory molecules (HLA-A2.1, β2 microglobulin, B7.1, CD70, ICAM-1 and LFA-3). These same CD8$^+$ cells are restimulated by two rounds of autologous, peptide-pulsed mononuclear cells, in the presence of IL-2 and IL-7. A non-specific expansion step with anti-CD3 mAb (OKT3) is also included to increase the total number of cells: generally 25-fold greater than that obtained at the end of the second restimulation step. Cytolytic T cell activity is measured against peptide-loaded T2 cells and a panel of A2$^+$ melanoma cells, while the purity of the in vitro-stimulated CD8$^+$ T cells is assessed by flow cytometry. Additionally, interferon-gamma production, in response to antigen-specific stimulation and peptide-specific tetrameric analysis, confirms the effector function and specificity of the generated CTLs, respectively.

Potency of CTLs Generated from Naïve CD8$^+$ T Cells Isolated from Melanoma Cancer Patients It has been demonstrated in melanoma patients that antigen-specific CTLs, isolated from peripheral blood samples, are part of a heterogeneous population of cells that range from low to high avidity for the specific peptide/MHC complex to which the TCR is directed. However, the vast majority of these CTLs are of low avidity, and only the CTLs with high avidity demonstrate significant tumor cell lysis.[21] In addition, tumor-infiltrating lymphocytes (TILs) have been isolated from tumor masses in patients with melanoma. The ex vivo expansion of these TILs in the presence of high-dose IL-2 has resulted in objective responses in melanoma patients; however, these responses were of short duration and the highly-reactive cloned T cells originating from the TILs failed to generate any complete responses.[16]

In contrast, CTLs generated ex vivo with Drosophila-xAPCs are potent, high-avidity, antigen-specific T cells capable of peptide-specific lysis (see, e.g., FIG. 1) and strong melanoma tumor cell killing. The reproducible generation of the CTLs, with strong cytolytic activity for tumor cells, is believed to be attributable to several contributing factors. First, CD8$^+$ purification with a peptide-specific, anti-CD8 monoclonal antibody selected for cells with a high density of CD8, while the antibody release in the presence of specific peptide, avoided non-specific stimulation of the T cells. Second, the highly-purified CD8$^+$ T cells (Table I) are stimulated with xAPCs presenting specific T-cell epitopes in the context of MHC molecules, where a high density of antigen presentation results in a potent primary T-cell immune response. The inclusion of multiple costimulation molecules on the APCs optimizes the T cell stimulation. Third, the restimulation steps incorporate autologous, mononuclear cells that have been loaded with the same melanoma-associated T cell epitopes used in the primary stimulation and provide a boost to the proliferating T cells. Finally, a single non-specific expansion step with OKT3, autologous feeder cells and low-dose IL-2 maintains the same percentage of antigen-specific T cells recorded at the end of the second restimulation step, while increasing the total number of T cells ~25-fold.

TABLE I

Purification of CD8⁺ Cells by Positive Selection and Analyzed by Flow Cytometry (data represents summary of total of 28 patients)

| Cell Type | PBMC (%) | (Range) | Post-selection (%) | (Range) |
|---|---|---|---|---|
| CD3⁺ T cells | 45 | (29-64) | 83 | (59-98) |
| CD4⁺ T cells | 27 | (16-46) | 2 | (0.5-4) |
| CD8⁺ T cells | 17 | (8-31) | 84 | (60-96) |
| CD14⁺ monocytes | 27 | (11-43) | 5 | (0.5-17) |
| CD15⁺/CD16⁺ neutrophils | 2 | (0.5-9) | 0.5 | (0.5-1) |
| CD16⁺/CD15⁻ NK cells | 15 | (8-47) | 8 | (2-20) |
| CD19 B cells | 1 | (0.5-2) | 1 | (0.5-3) |

This ex vivo xAPC CD8⁺ T cell stimulation protocol resulted in CTLs with potent tumor cell lysis, high avidity for the peptide/MHC complex, and antigen-specificity as assessed by enumeration with peptide-specific tetrameric molecules, interferon-gamma release in response to specific antigenic stimulus and specific tumor lysis.

Evaluation of CTL Therapy in Malignant Metastatic Melanoma from Previous Studies Two phase I trials and one phase II trials have been conducted, which involved a total of 55 subjects with Stage III or Stage IV melanoma. Study 1, "Autologous Cytotoxic T Lymphocytes (CD8⁺) Serially Cultured Ex Vivo with *Drosophila* Antigen Presenting Cells, Interleukin-2, Interleukin-7, then Adherent Monocytes, and Tyrosinase Peptide", was an open-label study in 10 Stage IV melanoma patients. The clinical endpoints were: 1) safety and tolerability of reinfused autologous CTLs after in vitro immunization; 2) determination of the kinetics of the infused CTLs in the systemic circulation by limiting dilution analysis; 3) whole body disposition of $^{111}$indium-labelled CTLs by radioscintigraphy; 4) cell composition of biopsied nodules by immunohistochemical analysis (CTLs, $T_H$, NK, B cells) and 5) regression of measurable lesions and duration of response over two months.[22]

In Study 2, "Pilot Study of Subcutaneous Interferon-Alpha with Infusion of *Drosophila* Cell Stimulated Autologous CD8⁺ Lymphocytes for the Treatment of Advanced Melanoma", a total of 15 Stage III/IV melanoma patients were infused with autologous CD8⁺ T cells on background maintenance therapy with IFNα-2b. CTL therapy was evaluated by: 1) monitoring the safety and toleration of the reinfused CTLs; 2) cell composition of biopsied nodules; 3) regression of measurable lesions and 4) duration of response over three months. Subjects who had stable disease or demonstrated a clinical response at the follow-up evaluation (four weeks after the first infusion) were offered a second-cycle of treatment. Eight (8) of the fifteen (15) subjects underwent a second cycle of CTL therapy, four (4) subjects entered a third cycle and one (1) subject was treated with four cycles of T cell therapy.[23]

In Study 3, "Randomized Phase II Trial of Subcutaneous Interferon-α-2b (IFN) and Interleukin-2 (IL-2) with or without Infusion of *Drosophila* Cell-stimulated Autologous CD8 Lymphocytes for the Treatment of Advanced Melanoma", a total of 30 Stage III/IV melanoma patients were treated with cytokines alone (IFNα and IL-2) or cytokines plus T cells. It was a randomized study in which patients entered the cytokines-only arm (Arm A) or cytokines plus T cells arm (Arm B). Patients who entered and progressed on Arm A were offered an opportunity to cross over to the cytokines plus T-cell arm (Arm C). The primary end point of this study was to compare the time to progression (TTP) of disease between the two groups (Arm A versus Arm B). Statistical significance was reached in TTP in patients entering Arm B versus those entering Arm A (FIG. 11). In patients who crossed over from Arm A to Arm C, statistical significance in TTP was also detected in patients receiving T cells. Safety and tolerability of IFNα and IL-2 at the doses and on the schedule prescribed were also monitored.[24]

Rationale for Use of Interferon-α-2b (IFN-α-2b)

Interferon-alpha (IFN-α) has a broad spectrum of immunomodulatory and antiproliferative effects in a variety of malignancies. It is believed that one mechanism of action of IFN-α is the upregulation of tumor antigen expression on melanoma cells. It has the ability to enhance the expression of immunologically important molecules on the surface of the tumor. These include the MHC antigens, accessory molecules, as well as tumor-associated antigens.[25-27] These immunomodulatory effects may improve the activity of the immune system, including both antibodies and lymphocytes, to recognize and attack tumor cells in vivo. Active, specific immunotherapy has demonstrated significant clinical responses in the treatment of disseminated melanoma. The results of immune function studies discussed above have demonstrated that melanoma vaccine treatment increases the frequency of anti-melanoma CTLs. It is believed that these two modalities of immunotherapy may act synergistically. A five (5) day course of IFN-α (10 MU/m²; subcutaneously) was included in Study 2, and the results of IHC stains of tissue demonstrated that the timing and dose was sufficient to upregulate both class I and melanoma-associated antigen expression in serial biopsy samples obtained from a single patient at the specified time frames. The same 5-day course in clinical study was included in Study 3.

Rationale for the Use of Interleukin-2

Human recombinant interleukin-2 (IL-2) is a lymphokine produced by recombinant DNA technology that has been shown to exhibit a variety of biological activities. IL-2 stimulates the immune system and exerts its biological effects following binding to specific receptors on the surface of target cells. In vitro, it has been shown to enhance T cell proliferation and lymphocyte cytotoxicity, induce the killer activity of both lymphokine-activated and natural killer cells, and induce interferon-gamma production. Administration of high-dose IL-2 to 283 patients produced a remission rate of 7% with 9 complete responses, and the patients remained disease free from 9 to greater than 91 months.[28] Although high-dose IL-2 appeared to be more effective than low-dose continuous infusions, high doses of IL-2 are also more toxic. The most common side effects were flu-like symptoms. The most severe side effects were hypotension, capillary leak syndrome, and reduced organ perfusion. Subcutaneous administration of low-dose IL-2 (at 3 MIU/day×28 days) was used in part of Study 3, to enhance and maintain the level of adoptively-transferred autologous T cells. It was added after a short course of IFN-α and immediately following the CTL infusion to enhance lymphocyte mitogenesis, lymphocyte cytotoxicity, and interferon-gamma production in an effort to maintain the antigen-specific T cells in vivo.

Adoptive Transfer of Lymphocytes Following a Non-Myeloablative Immunosuppressive Chemotherapy Regimen Mouse studies demonstrated that induction of immunosuppression with chemotherapy prior to the administration of T cells was essential to enable the adoptive transfer of lymphocytes to mediate maximal tumor regression[29,30]. Based on these studies, clinical protocols were initiated to treat patients with the adoptive transfer of lymphocytes following the application of a non-myeloablative chemotherapeutic regimen[16,31]. Non-myeloablative preparative regimens have been used to treat patients receiving allogeneic bone marrow transplants, and these regimens appear ideally suited to induce the transient immunosuppression that may enhance the effect of adoptively transferred T lymphocytes. A regimen of cyclophosphamide and fludarabine originally used in renal cell cancer patients receiving HLA-matched allotransplants[32] has recently been used in metastatic melanoma patients[16,31]. The rationale for the incorporation of a lymphodepleting regimen prior to adoptive transfer of T cells was to possibly destroy regulatory cells, disrupt homeostatic T cell regulation ("making space"), or abrogate other normal tolerogenic mechanisms which potentially could enhance the engraftment of the transferred T cells. No treatment-related mortality was observed, and therefore non-myeloablative chemotherapy in combination with antitumor lymphocytes plus high-dose IL-2 should be safe. The non-myeloablation was induced with fludarabine (25 mg/m$^2$) and cyclophosphamide (60 mg/kg) and was followed by a lymphocyte infusion and high dose IL-2 (720,000 IU/kg).

The combination of chemotherapeutic agents cyclophosphamide and fludarabine, while not completely myeloablative, has been demonstrated to be myelosuppressive, affecting neutrophils, lymphocytes, platelets, and red blood cells. Neutrophil levels, which fell to a nadir on day 10 following the initiation of chemotherapy, were recorded at 6/mm$^3$ and recovered to above 500/mm$^3$ on day 14 with support of filgrastim (G-CSF). Lymphocyte levels had a nadir of 6/mm$^3$ and recovered to above 200/mm$^3$ during the same time period. Patients usually displayed neutrophil counts above 500/mm$^3$ and platelet counts above 20,000/mm$^3$, 2-3 weeks after the initiation of the chemotherapy. No patients needed a stem cell transfusion to rescue marrow function, and therefore the overall treatment appears to be safe. However, CD4 counts did remain persistently low (the mean CD4 count at approximately day 200 was 156/mm$^3$, with a range between 46/mm$^3$ and 320/mm$^3$), which is a known side effect of the immunosuppression induced with fludarabine. The development of opportunistic infections did occur (i.e., transient herpes zoster outbreaks), which resolved following the termination of treatment.

Cladribine (2-CdA, Leustatin®), a purine analog similar to fludarabine, is approved for use in the treatment of hairy cell leukemia and has been evaluated also in multiple sclerosis (MS) patients in an effort to reduce autoreactive T lymphocytes. In MS patients a specific decrease in T cell subsets was correlated with different doses of cladribine.[33-35] It has a very favorable toxicity profile relative to other lymphocytolytic drugs, while inducing a long-lasting lymphopenia. Lymphocyte levels plunge immediately after the first infusion of cladribine, reach a nadir at 5 months and begin to recover by 6 months when administered for 4 monthly courses[33,34]. Lymphopenia was observed in all patients, and infectious complications were not a serious problem. The drug may be given by the convenient subcutaneous route without causing local irritation and with pharmacokinetic and therapeutic results that appear entirely equivalent to the IV route[36,37].

A recent study in humans identifying T regulatory cells ($T_{reg}$) as immunosuppressive in a vaccine setting demonstrated an enhanced antitumor immune response following depletion of the $T_{reg}$ subset which displays a CD4+/CD25+$^{hi}$ phenotype along with CD28, CTLA-4 and GITR.[38] This T cell subset can be selectively depleted (approximately 3 weeks) following a single dose of denileukin diftitix (DAB$_{389}$IL-2, ONTAK®). Four days following the single dose, 37-77% depletion of $T_{reg}$ cells was noted in eight (8) renal cell carcinoma patients. Following the T cell depletion, an RNA-DC vaccine was administered and a 10-fold enhancement in the immune response to the vaccine antigens was noted in the patients receiving both DAB IL-2 and vaccine versus vaccine alone. Thus, the same dose (18 μg/kg) six days prior to an adoptive transfer of the antigen-specific CTLs is a preferred dose for use in regimens in accordance with the invention.

Patient Selection

Subjects for the study are human patients diagnosed with metastatic melanoma who are HLA-A2 positive. A monoclonal antibody (BB7.2) is used to analyze PBMC samples by FACS analysis and further analysis is performed using the Olerup SSP™ PCR test (GenoVision) to determine the HLA-A*0201 subtype.

Treatment Schema

Figure 2:
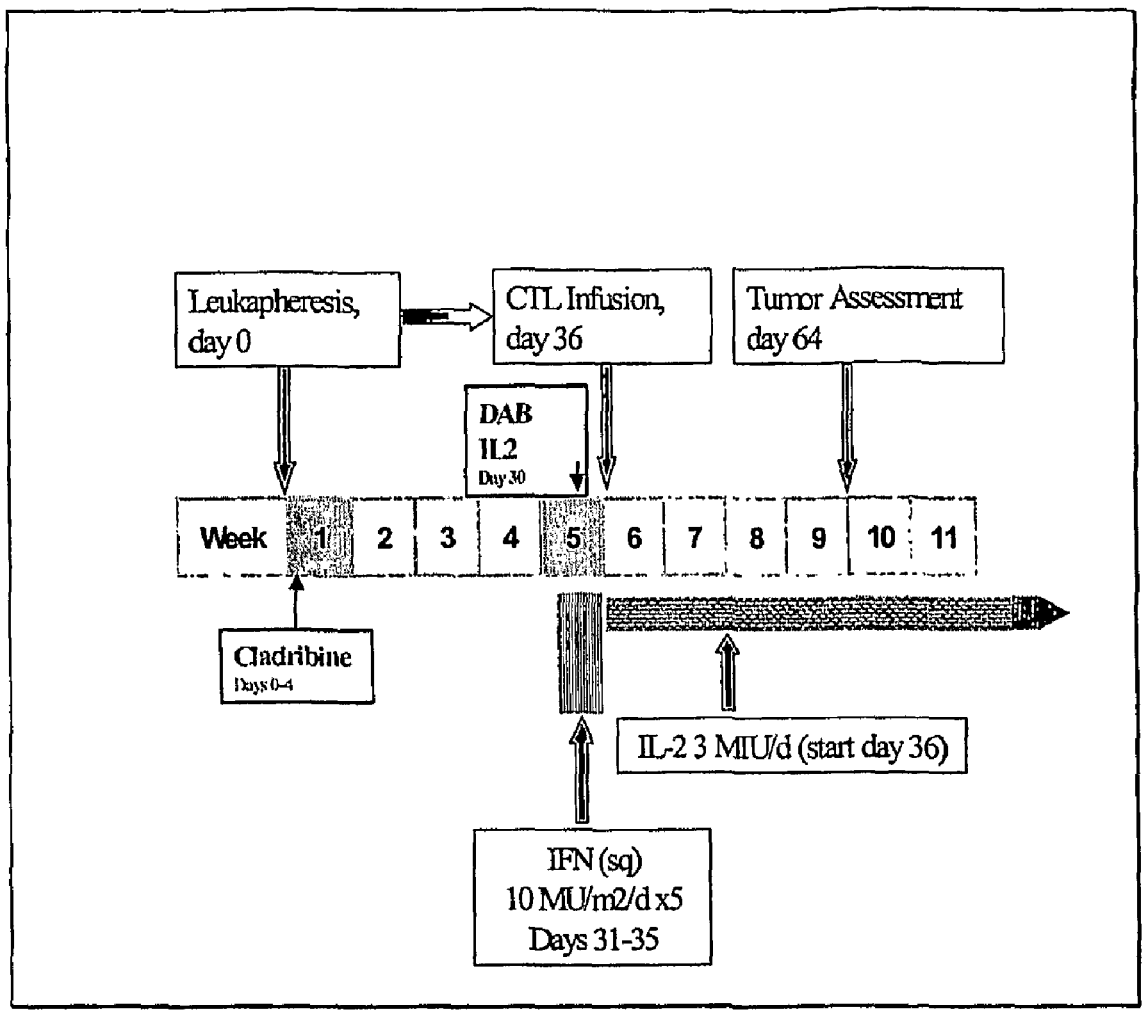
FIG. 2 provides a schematic illustration of two preferred embodiments of treatment regimens according to the invention along with a control regimen.

FIG. 2 depicts the treatment regimens described in more detail below. The patients are divided into three cohorts of subjects, with 10 in each cohort. In the Cohort A regimen, a control for the lymphodepleting regimen, CTLs plus cytokines are administered. In the Cohort B regimen, which is a preferred embodiment of the invention, patients receive cladribine (days 0-4) plus CTLs (day 36) plus cytokines. In the Cohort B regimen, which is another preferred embodiment of the invention, patients receive DAB IL-2 (day 30) plus CTLs (day 36) plus cytokines. The experimental regimens are described in more detail below.

CTLs Specific for Melanoma-Associated Antigens

Cytotoxic T lymphocyte therapy for malignant melanoma utilizes autologous in vitro-activated CD8$^+$ T cells to destroy melanoma cells bearing melanoma-associated antigenic epitopes. CTLs are prepared from leukapheresis samples generated at the clinical site and transferred to a facility where CTLs are generated under GMP guidelines and returned for infusion.

On day 0, patients with metastatic melanoma undergo leukapheresis (approximately 10-15 liter run, depending on the patient's weight and condition). The obtained cells are shipped overnight at room temperature for processing at a GMP manufacturing facility. At appropriate times, leukapheresis is performed to obtain peripheral blood lymphocytes for analysis. These samples are used to monitor the presence of antigen-specific T cells and the presence of circulating melanoma tumor cells. The monitoring leukapheresis procedure processes approximately 5 liters of peripheral blood (or one-third the volume collected at the initial leukapheresis to obtain CD8 cells for subsequent infusion) at the clinical site and is shipped to the GMP manufacturing facility. A PCR assay is used to determine a decrease in the level of circulating melanoma cells following therapy. The detection of circulating melanoma cells can be measured by a sensitive, quantitative real time PCR assay[39-41]. The presence of antigen-specific T cells is evaluated with peptide-specific/HLA-A2 tetramers.

The final CTL preparation for infusion contains 1×10$^{10}$ autologous CTLs in 300 mL, contained in 76% (v/v) Lactated Ringer's Solution, 4% (v/v) of D5NS and 20% (v/v) of 25% human serum albumin (HSA). The CTL product is prepared in a sterile bag, suitable for infusion, held on ice and infused over 30 minutes, within forty-two (42) hours of preparation.

Prior to infusion, the CTLs are monitored for lytic activity (both peptide-loaded target cells and melanoma tumor cell lysis), viability, and purity by FACS analysis. The absence of both *Drosophila* cell DNA and insect viral RNA is checked with sensitive quantitative, real-time PCR assays. Sterility is determined by BacT/Alert® analysis, mycoplasma testing and Gram stain analysis.

Patients receive a CTL infusion of approximately 10$^{10}$ autologous T cells, which have been stimulated and expanded ex vivo to become cytotoxic T lymphocytes capable of targeting to cells in vivo expressing the antigens to which the CTLs are directed. The cells are infused after the end of the IFN-alpha treatment and immediately precede the start of the IL-2 regimen.

Cytokines

Interleukin-2 (IL-2) is obtained from Chiron Corporation (Emeryville, Calif.). It is supplied as single-use vials containing 22 million IU (~1.3 mg) of IL-2 as a sterile, white to off-white lyophilized cake plus 50 mg mannitol and 0.18 mg sodium dodecyl sulfate, buffered with approximately 0.17 mg monobasic and 0.89 mg dibasic sodium phosphate to a pH of 7.5 (range 7.2 to 7.8). The powder is reconstituted with 1.2 mL of Sterile Water for Injection, USP, and the resultant concentration is 18 million IU/ml or 1.1 mg/mL. Intact vials are stored in the refrigerator (2°-8° C.) and protected from light. Reconstituted IL-2 is further diluted with 2.4 mL of D5% water. The final concentration (6 MU/mL), once drawn into plastic syringes, is good for 14 days after reconstitution, if kept refrigerated at 2-8° C. The final dilution of IL-2 is self-administered on an outpatient basis subcutaneously at a dose of 3 million units (3 MIU), initiating immediately following the CTL infusion and daily until disease progression.

INTRON-A® is obtained from Schering-Plough Corporation (Kenilworth, N.J.). This IFN-alpha-2b product is supplied either as a lyophilized powder or a solution for injection in sterile 5ml vials. A vial contains approximately $3 \times 10^6$ U or $18 \times 10^6$ U IFN. The lyophilized powder is reconstituted preferably just prior to use, as there is no bacteriostatic agent included; unused, lyophilized powder is stored in a refrigerator or freezer (−4° C. to −20° C.). When the agent is supplied as an injectable solution, it is stored in the refrigerator (2°-8° C. or 36°-46° F.). The final dilution of IFN-α is self-administered on an outpatient basis at 10 MU/m$^2$ on days 31-35 as a subcutaneous injection.

$DAB_{389}IL-2$ $DAB_{389}IL-2$ (denileukin diftitox, ONTAK®) is a recombinant DNA-derived cytotoxic protein composed of the amino acid sequences for diphtheria toxin fragments A and B followed by the sequences for interleukin 2 that is expressed in E coli. It is a targeted drug, which binds to cells expressing CD25 (IL-2R) on their surface. It interacts with the high-affinity IL-2 receptor on the surface of malignant or normal T regulatory ($T_{reg}$) cells to inhibit intracellular protein synthesis, rapidly leading to cell death. $DAB_{389}IL-2$ is supplied in single use vials as a sterile, frozen solution intended for intravenous (IV) administration. Each 2 mL vial of ONTAK contains 300 mcg of recombinant DAB-IL2 in a sterile solution of citric acid (20 nM), EDTA (0.05 mM) and polysorbate 20 (<1%) in water for injection, USP. The solution has a pH of 6.9-7.2. Intact vials are stored frozen or −10° C. but not refrozen. The material is brought to room temperature (25° C. or 77° F.) before preparing the dose by thawing in a refrigerator for not more than 24 hours or at room temperature for 1-2 hours, and diluted with NS to a concentration of >15 mcg/mL. $DAB_{389}IL-2$ is administered by intravenous injection, preferably by infusion over at least 15 minutes. Patients assigned to Cohort C receive a single subcutaneous injection of DAB IL-2 on day 30, which is one day before the initiation of IFN-α and six days prior to the injection of the CTLs. The dose is 18 µg/kg.

Cladribine

Leustatin® (2-chloro-2'deoxy-β-D-adenosine) is a synthetic antineoplastic agent. It is a purine nucleoside analog resistant to the action of adenosine deaminase, which results in preferential lymphocytoxicity. In cells with a high ratio of deoxycytidine kinase to deoxynucleotidase (e.g., lymphocytes and monocytes), cladribine is phosphorylated into the active triphosphate deoxynucleotide, 2-CdATP, which accumulates, causing a disruption of cellular metabolism, DNA damage, and subsequent cell death. The drug is a clear, colorless, sterile, preservative-free, isotonic solution supplied in single-use vials containing 10 mg (1 mg/mL) of cladribine. Each mL of cladribine contains 1 mg of the active ingredient and 9 mg (0.15 mEq) of sodium chloride as an inactive ingredient. The solution has a pH range of 5.5 to 8.0. Phosphoric acid and/or dibasic sodium phosphate may be added to adjust the pH to 6.3±0.3. Intact vials are stored refrigerated (2-8° C.). The dose of cladribine for Cohort B is 0.12 mg/kg/day for a total of 5 days, fractionated into 3-4 sites where a maximum of 3.0 cc is administered at a single site. The total cladribine dose is 0.6 mg/kg. (Cladribine, administered subcutaneously on this same schedule (5 consecutive days) and at a dose of 0.14 mg/kg/day (total dose=0.7 mg/kg) has been reported to be safe in hairy cell leukemia patients[37]. Additionally, the cladribine administered on this schedule and dose to sixty patients produced approximately 70% lymphodepletion after a single cycle with clinically safe myelosuppression. As a result of a change in standardization, Leustatin has been found to be 12% higher than reported in previous clinical studies compared with a cladribine stock synthesized in a laboratory. The dose that was reported to be 0.1 mg/kg is now estimated to actually have been only 0.087 mg/kg[33]. Regarding the safety of subcutaneous administration with the Leustatin® formulation fractionated into 2-3 sites, a study in relapsing-remitting multiple sclerosis patients used 0.07 mg/kg/day×5 days, monthly for 6 months for a total cumulative dose of 2.1 mg/kg[36]. A total of 27 patients randomized to the treatment drug arm. Infections were limited to an episode of mild segmental herpes zoster that occurred in two cladribine-treated patients and in one patient receiving placebo. There were no individual cases of significant thrombocytopenia, anemia granulocytopenia or generalized marrow suppression.)

Optional Supportive Care

Patients may receive any of the following to abrogate IFN-alpha and IL-2 toxicity during treatment and thereafter: acetaminophen (650 mg PO q4h prn), diphenhydramine (50 mg IM or PO q4h prn), indomethacin (25 mg PO TID or 75 mg SR qd), prochlorperazine (10 mg IV or PO q4h prn nausea), Zantac® (150 mg BID gastritis). Other anti-inflammatory and antiemetic agents not specifically prescribed may be substituted for any of the above supportive drugs.

Although the invention has been described in detail above in reference to illustrative examples and preferred embodiments, the artisan will understand that the scope of the invention is defined not by the foregoing description, but by the appended claims as properly construed under principles of patent law.

REFERENCES

1. Hryniuk W, Bush H. The importance of dose intensity in chemotherapy of metastatic breast cancer. *J Clin Oncol* 4:1162-1170, 1986.

2. Herzig, R H. Dose-intensive therapy for advanced melanoma. In: J. O. Armitage, K. H. Antman (eds.), *High-Dose Cancer Therapy, Pharmacology, Hematopoietins, Stem Cells*; Baltimore: Williams and Wilkins pp 750-754, 1992.

3. Mitchell M S, Harel W, Kan-Mitchell J, et al. Active specific immunotherapy of melanoma with allogeneic cell lysates: rationale, results and possible mechanisms of action. In: J.-C. Bystryn, S. Ferrone and P. Livingston (eds.), *Specific Immunotherapy of Cancer with Vaccines*; Ann. N.Y. Acad. Sci. pp 153-166, 1993.

4. Quan W D Y Jr, Mitchell M S. *Principles of biologic therapy*. In: C. M. Haskell, ed. Cancer Treatment; Philadelphia: W.B. Saunders pp 57-69, 1995.

5. Mitchell M S, Jakowatz J, Harel W, et al. Increased effectiveness of interferon-alfa 2b following active specific immunotherapy for melanoma. *J Clin Oncol* 12:402-411, 1994.

6. Van der Bruggen P, Traversari C, Chomez P, et al. A gene encoding an antigen recognized by cytolytic T lymphocytes on a human melanoma. *Science* 254:1643-1647, 1991.

7. Gaugler B, Van der Eynde B, Van der Bruggen P, et al. Human gene MAGE-3 codes for an antigen recognized on a melanoma by autologous cytolytic T lymphocytes. *J Exp Med* 179:921-930, 1994.

8. Kawakami Y, Eliyahu S, Sakaguchi K, et al. Identification of the immunodominant peptides of the MART-1 human melanoma antigen recognized by the majority of HLA-A2-restricted tumor infiltrating lymphocytes. *J Exp Med* 180:347-352, 1994.

9. Brichard V, Van Pel A, Wolfel T, et al. The tyrosinase gene codes for an antigen recognized by autologous cytolytic T lymphocytes on HLA-A2 melanomas. *J Exp Med* 178:489-495, 1993.

10. Robbins P F, el-Gamil M, Kawakami Y, Stevens E, Yannelli JR, Rosenberg SA. Recognition of tyrosinase by tumor-infiltrating lymphocytes from a patient responding to immunotherapy. *Cancer Res* 54:3124-3126, 1994.

11. Bakker A B, Schreurs M W, de Boer A J, et al. Melanocyte lineage-specific antigen gp100 is recognized by melanoma-derived tumor-infiltrating lymphocytes. *J Exp Med* 179:1005-1009, 1994.

12. Wolfel T, Van Pel A, Brichard V, et al. Two tyrosinase nonapeptides recognized on HLA-A2 melanoma by autologous cytolytic T lymphocytes. *Eur J Immnol* 24:759-764, 1994.

13. Visseren M J W, Van Elsas A, Van der Voort E I H, et al. CTL specific for the tyrosinase autoantigen can be induced from healthy donor blood to lyse melanoma cells. *J Immunol* 154:3991-3998, 1995.

14. Rubin J T, Lotze M T. Adoptive cellular immunotherapy of cancer. In: M. S. Mitchell (ed.), *Biological Approaches to Cancer Treatment. Biomodulation*; New York: McGraw-Hill pp 379-410, 1993.

15. Yee, C, Thompson, J A, Byrd, D, et al. Adoptive T cell therapy using antigen-specific CD8+ T cell clones from the treatment of patients with metastatic melanoma: In vivo persistence, migration and antitumor effect of transferred T cells. *PNAS* 99:16168-16173,2002.

16. Dudley M E, Wunderlich, J R, Robbins P F, et al. Cancer regression and autoimmunity in patients after clonal repopulation with antitumor lymphocytes. *Science* 298:850-854, 2002.

17. Oelke M, Maus M V, Didiano, D et al. Ex vivo induction and expansion of antigen-specific cytotoxic T cells by HLA-Ig-coated artificial antigen-presenting cells. *Nat Med* 9:619-624, 2003.

18. Leturcq D L, Richards J M, Jackson M R, Peterson P A and Moriarty A M. Ex Vivo Generation of Potent Cytotoxic T Lymphocytes for the Treatment of Cancer: A Novel Antigen Presentation System. *Society of Biological Therapy* 17th Annual Meeting; Abstract #40,2002.

19. Jackson M R, Song E S, Yang Y, et al. Empty and peptide-containing conformers of class I major histocompatibility complex molecules expressed in *Drosophila melanogaster* cells. *Proc Natl Acad Sci, USA* 89:12117-12121, 1992.

20. Cai Z, Brunmark A, Luxembourg A T, et al. Probing the activation requirements for naïve CD8+ T cells with *Drosophila* cell transfectants as antigen presenting cells. *Immunol Rev* 165:249-265, 1998.

21. Yee, C., Savage, P. A., Lee, P. P et al. Isolation of high avidity melanoma-reactive CTL from heterogeneous populations using peptide-MHC tetramer. *J Immunol* 162:227-2234, 1999.

22. Mitchell M S, Darrah D, Yeung D et al. Phase I trial of adoptive immunotherapy with cytolytic T lymphocytes immunized against a tyrosinase epitope. *J Clin Oncol* 20:1075-1086, 2002.

23. Richards J M, Moriarty A M, Leturcq D L, Jackson M R and Peterson P A. Treatment of advanced malignant melanoma with ex vivo-generated autologous T cells with specificity for melanoma-associated target antigens. *ASCO Annual Meeting*, San Francisco, Calif., May 2001.

24. Richards J M, Moriarty A M, Leturcq D L et al. Treatment of advanced malignant melanoma with autolgous, ex vivo-generated T cells with specificity for melanoma-associated target antigens. *ASCO Annual Meeting*, Chicago, Ill., June 2003.

25. Dorval, T, Palangies, T, Jouve M et al. Clinical phase II trial of recombinant DNA interferon (interferon alpha 2b) in patients with metastatic malignant melanoma. *Cancer* 58:215-218, 1986.

26. Sertoli M R, Bernengo M G, Ardizzoni A, et al. Phase II trial of recombinant alpha-2b interferon in the treatment of metastatic skin melanoma. *Oncology* 46:96-98, 1989.

27. Robincon W A, Mughal T I, Thormas M R, et al. Treatment of metastatic mealignant melanoma with recombinant interferon alpha 2. *Immunobiology* 172:275-282, 1986.

28. Rosenberg, S A, Yang J C, Topalian S L, et al. Treatment of 283 consecutive patients with metastatic melanoma or renal cell cancer using high-dose bolus interleukin-2. *JAMA* 271:907-9113, 1994.

29. North, R J. Cyclophosphamide-facilitated adoptive immunotherapy of an established tumor depends on the elimination of tumor induced suppressor cells. *J Exp Med* 155:1063-1074.

30. Mills, C. D., and North, R. J.: Expression of passively transferred immunity against an established tumor depends on generation of cytolytic T cells in recipient. *J Exp Med* 157:1448-1460, 1983.

31. Dudley, M., J. Wunderlich, J. C. Yang, et al. A Phase I study of non-myeloablative chemotherapy and adoptive transfer of autologous tumor antigen-specific T lymphocytes inpatients with metastatic melanoma. *J Immunother* 25:243-251, 2002.

32. Childs, Chernoff, A., Contentin, N. et al. Regression of metastatic renal-cell carcinoma after nonmyeloablative allogeneic peripheral-blood stem-cell transplantation. *NEJM* 343:750-758, 2000.

33. Beutler, E. et al. Marrow suppression produced by repeated doses of cladribine. *Acta Haematol* 91:10-15, 1994.

34. Beutler, E. et al. The treatment of chronic progressive multiple sclerosis with cladribine. *Proc Natl Acad Sci USA* 93:1716-1720, 1996.

35. Rice, G P A et al. Cladribine and progressive MS: Clinical and MRI outcomes of a multicenter controlled trial. *Neurology* 54:1145-1155, 2000.

36. Romine, J S, Sipe, J C, Koziol, J A et al. A double-blind, placebo-controlled, reandomized trial of cladribine in relapsing-remitting multiple sclerosis. *Proc Assoc Amer Physicians* 111:35-44, 1999.

37. von Rohr, A, Schmitz, S-F H, Tichelli, A et al. Treatment of hairy cell leukemia with cladribine (2-chlorodeoxyadenosine) by subcutaneous bolus injection: a phase II study. *Annals of Oncology* 13:1641-1649, 2002.

38. View, J, Su, Z, and Dannull, J. Enhancement of antitumor immunity following depletion of CD4+CD25+ regulatory T cells. *Annual Meeting Proceedings ASCO* Abst 2506, 2004.

39. Keilholz, U., Goldin-Lang, P, Bechrakis, N E et al. Quantitative detection of circulating tumor cells in cutaneous and ocular melanoma and quality assessment by real-time reverse transcriptase-polymerase chain reaction. *Clinical Cancer Research* 10:1605-1612, 2004.

40. Hoon, D S B, Bostick, P, Kuo, C et al. Molecular markers in blood as surrogate prognostic indicators of melanoma recurrence. *Cancer Research* 60:2253-2257, 2000.

41. Goydos, J S and Reintgen, D S. A molecular technique useful in the detection of occult metastases in patients with melanoma. In: B. J. Nickoloff (ed.) *Methods in Molecular Medicine Vol* 61: *Melanoma: Methods and Protocols*; Totowa, N.J.: Humana Press pp. 301-320.

What is claimed is:

1. A method for treating a subject in need of treatment for cancer, comprising:
   (a) obtaining naïve CD8+T cells from the subject;
   (b) contacting the naive CD8+T cells ex vivo with xenogenic antigen presenting cells loaded with one or more peptide antigens, thereby generating activated CTLs that target cells expressing said one or more peptide antigens;
   (c) administering to the subject the activated CTLs;
   (d) administering to the subject at least two cytokines that effect CTL persistence; and
   (e) administering to the subject a lymphodepleting agent selected from the group consisting of cladribine and denileukin diftitox.

2. A method as defined in claim 1, wherein said at said at least two cytokines comprise interferon-α-2b and interleukin-2.

3. A method as defined in claim 2, wherein said one or more peptide antigens comprise an amino acid sequence derived from a protein selected from gp100, tyrosinase, and MART-1.

4. A method as defined in claim 1, wherein said one or more peptide antigens consists of peptide antigens derived from human gp100, tyrosinase, and MART-1 proteins.

5. A method as defined in claim 1, wherein each of said one or more peptide antigens is selected from the group consisting of YMNGTMSQV (SEQ ID NO:1), YMDGTMSQV (SEQ ID NO:2), AAGIGILTV (SEQ ID NO:3), ITDQVPFSV (SEQ ID NO:4), YLEPGPVTA (SEQ ID NO:5), and KTWGQYWQV (SEQ ID NO:6).

6. A method as defined in claim 5, wherein said cancer is a melanoma.

7. A method as defined in claim 1, wherein the administration of the lymphodepleting agent begins before the administration of the activated CTLs.

* * * * *

```
                        SEQUENCE LISTING

<160> NUMBER OF SEQ ID NOS: 76

<210> SEQ ID NO 1
<211> LENGTH: 9
<212> TYPE: PRT
<213> ORGANISM: Homo sapiens

<400> SEQUENCE: 1

Tyr Met Asn Gly Thr Met Ser Gln Val
1               5

<210> SEQ ID NO 2
<211> LENGTH: 9
<212> TYPE: PRT
<213> ORGANISM: Homo sapiens

<400> SEQUENCE: 2

Tyr Met Asp Gly Thr Met Ser Gln Val
1               5

<210> SEQ ID NO 3
<211> LENGTH: 9
<212> TYPE: PRT
<213> ORGANISM: Homo sapiens

<400> SEQUENCE: 3

Ala Ala Gly Ile Gly Ile Leu Thr Val
1               5

<210> SEQ ID NO 4
<211> LENGTH: 9
<212> TYPE: PRT
<213> ORGANISM: Homo sapiens

<400> SEQUENCE: 4

Ile Thr Asp Gln Val Pro Phe Ser Val
1               5

<210> SEQ ID NO 5
<211> LENGTH: 9
<212> TYPE: PRT
<213> ORGANISM: Homo sapiens

<400> SEQUENCE: 5

Tyr Leu Glu Pro Gly Pro Val Thr Ala
1               5

<210> SEQ ID NO 6
<211> LENGTH: 9
<212> TYPE: PRT
<213> ORGANISM: Homo sapiens

<400> SEQUENCE: 6
```

```
Lys Thr Trp Gly Gln Tyr Trp Gln Val
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Thr Asp Gln Val Pro Phe Ser Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Leu Glu Pro Gly Pro Val Thr Ala
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Gly Ile Gly Ile Leu Thr Val
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Leu Ala Gly Ile Gly Ile Leu Thr Val
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Leu Thr Ser Thr Val Gln Leu Val
1               5

<210> SEQ ID NO 12
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 12

His Leu Tyr Gln Gly Cys Gln Val Val
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ile Phe Gly Ser Leu Ala Phe Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Ile Ser Ala Val Val Gly Ile Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Leu Thr Ser Ile Ile Ser Ala Val
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Met Ala Gly Val Gly Ser Pro Tyr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Leu Val Lys Ser Pro Asn His Val
1               5

<210> SEQ ID NO 18
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Leu Val Ser Glu Phe Ser Arg Met
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Leu Ser Gly Ala Asn Leu Asn Leu
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Leu Thr Pro Leu Pro Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Leu Leu Met Trp Ile Thr Gln Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Leu Phe Ala Gly Pro Pro Val
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Leu Glu Thr Phe Arg Glu Gln Val
```

```
<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Leu Gln Ser Pro Lys Ser Pro Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Leu Leu Lys Leu Arg Arg Pro Val
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Leu Tyr Ile Pro Ser Val Asp Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Leu Leu Met Trp Ile Thr Gln Val
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Leu Ala Lys Phe Leu His Trp Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 29

Ser Thr Ala Pro Pro Val His Asn Val
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Leu Trp Gly Pro Arg Ala Leu Val
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Met Trp Gly Asn Leu Thr Leu Ala
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Leu Val Asp Asp Phe Leu Leu Val
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Leu Ser Thr Ala Phe Ala Arg Val
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Leu Ser Leu Leu Met Trp Ile Thr
1               5

<210> SEQ ID NO 35
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 35

Glu Leu Trp Thr His Ser Tyr Lys Val
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Val Ala Glu Leu Val His Phe Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Ile Phe Ala Thr Cys Leu Gly Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Leu Tyr Ile Phe Ala Thr Cys Leu
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Leu Met Ala Gln Glu Ala Leu Ala Phe Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Thr Leu Glu Lys Ile Asn Lys Thr
1               5
```

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Lys Ala Ser Glu Lys Ile Phe Tyr Val
1               5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Ser Leu Leu Met Trp Ile Thr Gln Cys Phe Leu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Glu Leu Thr Leu Gly Glu Phe Leu Lys Leu
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Leu Thr Leu Gly Glu Phe Leu Lys Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Ser Leu Leu Glu Lys Arg Glu Lys Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

```
Thr Leu Gly Glu Asp Asp Pro Trp Leu
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Leu Gly Leu Lys Pro Leu Glu Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Leu Trp Thr Ser Ala Lys Asn Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Thr Ala Pro Pro Ala His Gly Val
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Met Gly Ser Glu Glu Leu Arg Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Leu Gly Ser Pro Val Leu Gly Leu
1               5

<210> SEQ ID NO 52
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 52

Tyr Leu Phe Phe Tyr Arg Lys Ser Val
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Gln Gln Glu Glu Thr Phe Leu Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Leu Ala Lys Phe Ser Pro Tyr Leu
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Leu Thr His Val Leu Tyr Pro Val
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Thr Phe Lys Asn Trp Pro Phe Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Leu Leu Gln His Leu Ile Gly Leu
1               5

<210> SEQ ID NO 58
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Leu Asp Gln Arg Val Phe Phe Val
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Leu Asp Gln Arg Val Phe Val Val
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Phe Leu Asp Gln Val Ala Phe Val Val
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Leu Asp Arg Glu Gln Leu Tyr Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Met Gln His Leu Leu Ser Pro Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Thr His Gly Ile Thr Arg Leu
```

```
<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Gln Pro Leu Ser Gly Pro Gly Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Leu Asp Arg Asp Ser Leu Tyr Val
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Leu Tyr Leu Glu Leu Ser Gln Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Val Leu Glu Tyr Val Ile Lys Val
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Val Ala Asp Leu Val Gly Phe Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 69

Lys Thr Trp Gly Gln Tyr Trp Gln Val
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ile Leu Ser Leu Lys Glu Ala Ser Thr
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Met Ala Ser Arg Ser Met Arg Leu
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Leu Ala Leu Ala Ala Leu Leu Val Val
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Leu Leu Val Val Asp Arg Glu Val
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Met Asn Gly Thr Met Ser Gln Val
1               5

<210> SEQ ID NO 75
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 75

Tyr Met Asp Gly Thr Met Ser Gln Val
1               5

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Ala Glu Gly Leu Asp Thr Gln Arg Phe Ser Gly
1               5                   10
```